United States Patent
Marten et al.

(10) Patent No.: US 8,709,080 B2
(45) Date of Patent: Apr. 29, 2014

(54) COATED DEVICES COMPRISING A FIBER MESH IMBEDDED IN THE DEVICE WALLS

(75) Inventors: Lewis H. Marten, Westwood, MA (US); Dennis Creedon, Sandwich, MA (US); Christopher Vettori, Marshfield, MA (US)

(73) Assignee: E. Benson Hood Laboratories, Pembroke, MA (US)

( * ) Notice: Subject to any disclaimer, the term of this patent is extended or adjusted under 35 U.S.C. 154(b) by 608 days.

(21) Appl. No.: 12/559,570

(22) Filed: Sep. 15, 2009

(65) Prior Publication Data

US 2010/0076555 A1    Mar. 25, 2010

Related U.S. Application Data

(60) Provisional application No. 61/098,488, filed on Sep. 19, 2008.

(51) Int. Cl.
*A61F 2/20*    (2006.01)

(52) U.S. Cl.
USPC ............................................................. 623/9

(58) Field of Classification Search
USPC .......................................... 623/9, 1.35–1.54
See application file for complete search history.

(56) References Cited

U.S. PATENT DOCUMENTS

| | | | |
|---|---|---|---|
| 3,562,820 A * | 2/1971 | Braun ........................ | 623/23.64 |
| 5,127,919 A * | 7/1992 | Ibrahim et al. ............... | 623/1.51 |
| 5,433,747 A * | 7/1995 | Grundei ........................... | 623/9 |
| 5,443,499 A * | 8/1995 | Schmitt ........................ | 623/1.49 |
| 5,527,353 A * | 6/1996 | Schmitt ........................ | 623/1.44 |
| 5,800,514 A * | 9/1998 | Nunez et al. ................. | 623/1.51 |
| 5,990,378 A * | 11/1999 | Ellis ........................... | 623/11.11 |
| 6,187,033 B1 * | 2/2001 | Schmitt et al. ............... | 623/1.35 |
| 7,084,082 B1 * | 8/2006 | Shimizu ........................ | 442/123 |
| 2004/0148032 A1 * | 7/2004 | Rutter et al. ................. | 623/23.7 |
| 2004/0220664 A1 * | 11/2004 | Chobotov ..................... | 623/1.23 |
| 2005/0163954 A1 * | 7/2005 | Shaw ............................. | 428/36.1 |
| 2006/0178739 A1 * | 8/2006 | Shalaby et al. .............. | 623/1.49 |
| 2006/0271165 A1 * | 11/2006 | Yip et al. ...................... | 623/1.16 |
| 2007/0073383 A1 * | 3/2007 | Yip et al. ...................... | 623/1.16 |
| 2007/0129791 A1 * | 6/2007 | Balaji ........................... | 623/1.44 |
| 2007/0167955 A1 * | 7/2007 | Arnault De La Menardiere et al. ............................... | 606/108 |
| 2007/0207186 A1 * | 9/2007 | Scanlon et al. ............... | 424/424 |
| 2007/0276486 A1 * | 11/2007 | Marten et al. ..................... | 623/9 |
| 2008/0069858 A1 * | 3/2008 | Weber ........................... | 424/426 |
| 2009/0187240 A1 * | 7/2009 | Clerc et al. ................... | 623/1.17 |

\* cited by examiner

*Primary Examiner* — Suzette J Gherbi
(74) *Attorney, Agent, or Firm* — Frommer Lawrence & Haug LLP; Ronald R. Santucci

(57) ABSTRACT

Devices used in the management of bodily airways including bronchial and tracheal stents, bronchial Y-tubes, bronchial TY-tubes, nasal septal buttons, and nasal stents. The present invention also relates to devices used to manage the esophagus, such as salivary bypass tubes. These devices may comprise a fiber mesh imbedded in the walls of the device in order to provide integrity to the device wall and permit anchoring and suturing of the device.

57 Claims, 28 Drawing Sheets

Mesh of fibers     Protective Coating

Mesh of fibers  Protective Coating

Mesh of fibers     Protective Coating

Mesh of fibers   Protective Coating

Mesh of fibers     Protective Coating

Mesh of fibers

Protective Coating

|  Mesh of fibers |  Protective Coating |

Mesh of fibers  Protective Coating

Mesh of fibers   Protective Coating

Mesh of fibers     Protective Coating

Mesh of fibers     Protective Coating

Mesh of fibers     Protective Coating

Mesh of fibers

Mesh of fibers      Protective Coating

Mesh of fibers      Protective Coating

Mesh of fibers
 Protective Coating

Mesh of fibers       Protective Coating

US 8,709,080 B2

COATED DEVICES COMPRISING A FIBER MESH IMBEDDED IN THE DEVICE WALLS

This application claims priority benefits of U.S. Provisional Patent Application No. 61/098,488 filed Sep. 19, 2008, the entire contents of which are hereby incorporated by reference.

INCORPORATION BY REFERENCE

The foregoing application, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to devices used in the management of bodily airways including bronchial and tracheal stents, bronchial Y-tubes, bronchial TY-tubes, nasal septal buttons, and nasal stents. The present invention also relates to devices used to manage the esophagus, such as salivary bypass tubes. These devices may comprise a fiber mesh imbedded in the walls of the device in order to provide integrity to the device wall and permit anchoring and suturing of the device.

BACKGROUND OF THE INVENTION

Devices may be used to manage organs that facilitate the passage of air or food in the body. In particular, airway management devices are used to assist in speaking and breathing following a laryngectomy, promote healing in the patient, provide an access point for forced ventilation of a patient, and act as a conduit for supplying oxygen to augment normal breathing. Examples of such devices include bronchial and tracheal stents, tracheal T-tubes, and tracheal Y-stents, which can be used in conjunction with a tracheostomy tube.

Bronchial and tracheal stents are prostheses that relieve an area of obstruction in the airways that lead to each lung. These stents are also used to prevent encroachment of masses, such as a tumour, into the airway.

Nasal septal buttons are devices which are inserted to close off a hole or aperture that may have formed in a medical patient's nasal septum as a result of a secondary infection resulting from an infectious disease like tuberculosis, nasal trauma, septal surgery, or the like.

Nasal splints are often used to relieve obstructions in the nasal cavity that may occur, for example, following surgery of the nasal cavity and paranasal sinuses. Nasal splints are inserted after nasal surgery on turbinates, the polyps (polypectomy), the septum (septoplasty), and after sinus surgery. The splints offer an airway (if the design incorporates a lumen, or tube); reduce, prevent or treat, the occurrence of synechiae formation (granulation); prevent adhesions of tissues or membranes within the nasal cavity, and control bleeding.

Devices can also be used to manage the esophagus. One example is a salivary bypass tube, which can stent the esophagus and prevent encroachment of masses such as tumours or salivary fistulas that grow in the tracheo-esophogeal wall.

However, delivery and positioning of these devices in airways or the esophagus may be difficult. These devices may require being sutured in place, especially if precise positioning is necessary, and are often comprised of material such as silicone rubber that may tear when a suture is passed through its wall. Further, these devices are often plagued by granulation, crusting and mucus build up, and such devices are at risk of compromising bodily walls. In addition, devices, especially those for airway management, can be difficult for the patient to clean and maintain, and ease of insertion and removal of complementary devices such as tubes can be hampered by the build up or encrustation of bodily fluids or by device fit friction.

SUMMARY OF THE INVENTION

The present invention is directed to airway or esophageal management devices which may be sutured into place without risk of tearing, and which may prevent the accumulation of mucus, crusting and granulation.

One aspect of the present invention is directed to an airway or esophageal management device comprising a fiber mesh imbedded in one or more portions of the device wall. In certain embodiments, the airway management device may comprise a tubular arm comprising: (i) a first open end; (ii) a second open end; (iii) a lumen extending therethrough having an inner surface and an inner circumference; (iv) an outer surface; (v) an outer circumference; (vi) a tubular wall between the inner surface and outer surface; and (vii) a longitudinal axis through the center of the lumen of the first tubular arm. In some embodiments, the fibers may be woven. In further embodiments, the woven fibers may be polyester or nylon.

In some embodiments, the airway or esophageal management device may further comprise a protective coating on one or more portions of the inner surface, one or more portions on the outer surface, or a combination thereof. In certain embodiments, the protective coating may be a polymeric coating. In further embodiments, the polymer may be parylene.

In additional embodiments, the airway or esophageal management device may further comprise an additional means to prevent movement or displacement of the device. In certain embodiments, the means to prevent movement or displacement of the device may be one or more rings around the circumference of the device, one or more posts that extend outwardly from the outer surface of the device, or a combination thereof. In some embodiments, the one or more rings may be located on the first open end of the device, the second open end of the device, between the first open end and the second open end of the device, or any combination thereof. In further embodiments, the posts may be cylindrical, cubic, pyramidal, or prism-shaped. In yet further embodiments, the posts may be distributed randomly or in a pattern along the outer surface of the device.

In some embodiments, the outer circumference of the first tubular arm may be constant throughout the arm. In other embodiments, the outer circumference may vary throughout the arm. In certain embodiments, the outer circumference may be greater near the first open end and the second open end, as compared to between the first open end and the second open end.

In some embodiments, the inner circumference of the airway management device may be constant throughout the device. In other embodiments, the inner circumference may vary throughout the device.

In some embodiments, the airway management device may further comprise a funnel attached to the second open end.

In additional embodiments, the airway or esophageal management device may further comprise a second tubular arm, wherein the second tubular arm comprises: (i) a first open end; (ii) a second open end; (iii) a lumen extending therethrough having an inner surface and an inner circumference; (iv) an outer surface; (v) an outer circumference; (vi) a tubular wall between the inner surface and outer surface; and (vii) a longitudinal axis through the center of the lumen of the second tubular arm. The second tubular arm may be connected to the first tubular arm between the first open end and the second open end of the first tubular arm. In some embodiments, the lumen of the first tubular arm and the lumen of the second tubular arm are continuous.

The second tubular arm may comprise a fiber mesh imbedded in one or more portions of the tubular wall of the second tubular arm. In some embodiments, the fibers may be woven. In further embodiments, the woven fibers may be polyester or nylon.

The second tubular arm may further comprise a protective coating on one or more portions of the inner surface, one or more portions on the outer surface, or a combination thereof, of the second tubular arm. In some embodiments, the protective coating may be a polymeric coating. In further embodiments, the polymer is parylene.

In some embodiments, the second tubular arm may further comprise a plug that connects to the second end of the second tubular arm. In certain embodiments, the plug may fit tightly adjacent to the inner surface of the second end of the second tubular arm.

In certain embodiments, the longitudinal axis of the first tubular arm may form an angle with the longitudinal axis of the second tubular arm. In some embodiments, the angle is between 0° and 180°. In further embodiments, the angle is 90°.

In additional embodiments, the second end of the first tubular arm may be bifurcated into a first tubular diagonal arm and a second tubular diagonal arm, wherein each arm comprises: (i) a first open end; (ii) a second open end; (iii) a lumen extending therethrough having an inner surface and an inner circumference; (iv) an outer surface; (v) an outer circumference; and (vi) a tubular wall between the inner surface and outer surface, and (vii) a longitudinal axis through the center of the lumen of each diagonal arm. In certain embodiments, the lumen in the diagonal arms is continuous with the lumen of the stent. In some embodiments, the lengths of the first diagonal arm and the second diagonal arm are equal. In other embodiments, the lengths of the first diagonal arm and the second diagonal arm are unequal.

In further embodiments, the first and/or second tubular diagonal arms may comprise a fiber mesh imbedded in one or more portions of the tubular wall. In certain embodiments, the fibers may be woven. In some embodiments, the woven fibers may be polyester or nylon.

In additional embodiments, the first and/or second tubular diagonal arms may comprise a protective coating on one or more portions of the inner surface, the outer surface, or both. In certain embodiments, the protective coating may be a polymeric coating. In some embodiments, the polymer may be parylene.

In certain embodiments, the longitudinal axis of the first tubular arm may form a first angle with the longitudinal axis of the first diagonal arm and the longitudinal axis of the first tubular arm may form a second angle with the longitudinal axis of the second tubular diagonal arm. In some embodiments, the first angle and the second angle may be equal. In other embodiments, the first angle and the second angle may be unequal.

In further embodiments, the airway or esophageal management device may comprise a bifurcated second end forming first and second tubular diagonal arms as described above, and may further comprise a second tubular arm as described above. In some embodiments, the lumen of the first tubular arm, the lumen of the first and second tubular diagonal arms, and the lumen of the second tubular arm may be all continuous.

Another aspect of the present invention relates to a nasal septal button. In certain embodiments, the nasal septal button may comprise (i) a first disc comprising a first surface, a second surface, and a disc wall therebetween; (ii) a second disc comprising a first surface, a second surface, and a disc wall therebetween; and (iii) a connection extending between the second surface of the first disc and the first surface of the second disc. A fiber mesh may be imbedded therein is imbedded therein one or more one or more portions of the wall of the first disc, the wall of the second disc, or a combination thereof. In some embodiments, the fibers may be woven. In further embodiments, the woven fibers may be polyester.

In additional embodiments, the nasal septal button may further comprise a protective coating on one or more portions of the top surface of the first disc, one or more portions of the second surface of the first disc, one or more portions of the first surface of the second disc, one or more portions of the second surface of the second disc, or a combination thereof. In some embodiments, the protective coating may be a polymeric coating. In certain embodiments, the polymer may be parylene.

In further embodiments, the first surface of the first disc of the nasal septal button may be convex and the second surface of the first disc may be concave. In certain embodiments, the first surface of the second disc may be concave and the second surface of the second disc may be convex.

In some embodiments, the connection of the nasal septal button may be attached to the center of the first disc and second disc.

In certain embodiments, the first disc and the second disc may be circular.

Yet, another aspect of the present invention is a nasal splint. In some embodiments, the nasal splint may comprise an oblong-shaped base comprising a first curved end, a second curved end, and a middle region therebetween wherein middle region comprises a first edge and a second edge, a first surface, and a second surface, wherein a fiber mesh is imbedded in one or more portions of the base. In certain embodiments, the fibers may be woven. In further embodiments, the woven fibers are polyester or nylon.

In additional embodiments, the nasal splint may further comprise a protective coating that covers one or more portions of the first surface, second surface, or both the first and second surfaces. The protective coating may be a polymeric coating. In some embodiments, the polymer may be parylene.

In further embodiments, the first edge of the middle region of the nasal splint is curved or substantially straight. In certain embodiments, the first edge of the middle region may further comprise a dorsal fin-shaped portion extending from the curvature of the first edge. In some embodiments, the second edge of the middle region may be curved or substantially straight.

In additional embodiments, the nasal splint may further comprise a tubular structure on the first surface of the base, wherein the tubular structure extends between the first end of the base and the second end of the base, and wherein the tubular structure comprises: (i) a first open end; (ii) a second open end; (iii) a lumen extending therethrough having an inner surface and an inner circumference; (iv) an outer surface; (v) an outer circumference; and (vi) a tubular wall between the inner surface and outer surface.

In some embodiments, the tubular structure may be adjacent to the first edge of the middle region of the base, the second edge of the middle region of the base, or is in the center of the base. In certain embodiments, the first end of the tubular structure and the second end of the tubular structure may be curved. In further embodiments, the tubular structure between the first and the second end may be curved.

In certain embodiments, the fiber mesh is imbedded in one or more portions of the tubular wall of the tubular structure. In some embodiments, the fibers may be woven. In additional embodiments, the woven fibers may be polyester or nylon.

In further embodiments, the tubular structure may further comprise a protective coating that covers one or more portions of the inner surface, outer surface, or both the inner surface and outer surface, of the tubular structure. In some embodiments, the protective coating may be a polymeric coating. In certain embodiments, the polymer may be parylene.

In additional embodiments, the tubular structure may further comprise a substantially flat segment that extends from the tube and is parallel to the base.

The various features of novelty which characterize the invention are pointed out in particularity in the claims annexed to and forming a part of this disclosure. For a better understanding of the invention, its operating advantages and specific objects attained by its uses, reference is made to the accompanying descriptive matter in which preferred embodiments of the invention are illustrated.

BRIEF DESCRIPTION OF THE DRAWINGS

For a more complete understanding of the invention, reference is made to the following description and accompanying drawings, in which.

DESCRIPTION OF THE INVENTION

Figure 1:
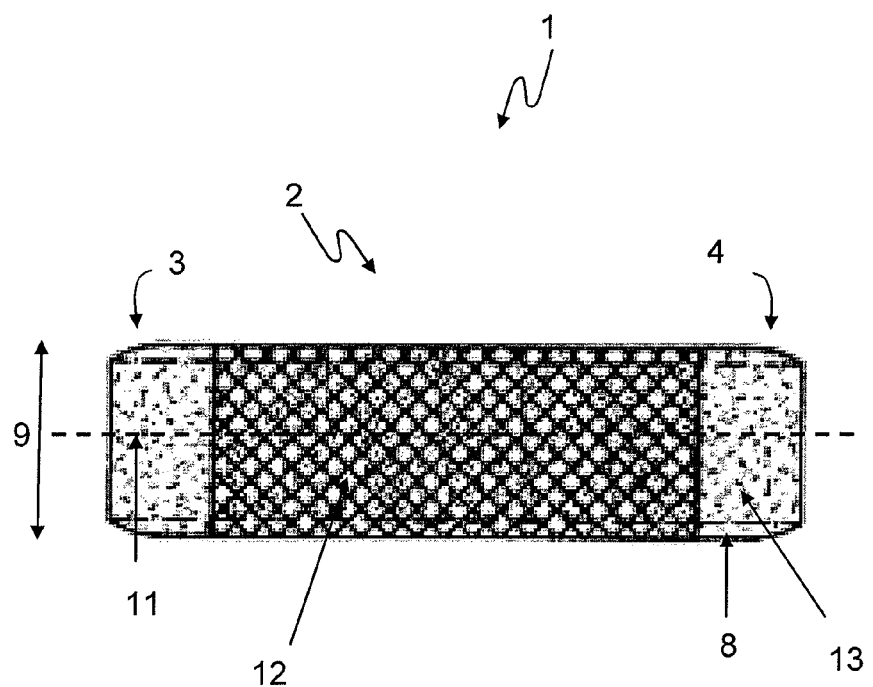
FIG. 1 is a side view of an airway management device according to one aspect of the present invention.
Figure 1:
Figure 1:

The present invention is directed to airway or esophageal management devices comprising a fiber mesh imbedded into their walls. The mesh allows the device to be sutured in place, reducing the possibility of tearing the device. The mesh provides an appropriate degree of integrity to the device wall, and a means of anchoring and suturing the device.

Importantly, the mesh is soft and flexible, and does not hinder the flexibility of device or the device wall. Hence, devices comprising the mesh still maintain their ability to be folded prior to their introduction into the airway/esophagus, their ability to conform to the airway/esophagus without compromising the function of the device or the airway/esophagus that is being treated.

These fibers may be a polymer such as polyester, polyethylene, nylon, polystyrene, polypropylene, Bakelite, neoprene, polyvinyl chloride, polyacrylonitrile, polyvinyl butyral, and other thermoplastics, thermosets, and elastomers known in the art. The mesh may be in the form of small open triangles, squares, pentagons, hexagons, and other polygons known in the art. The area of each shape may be between about 0.01 mm$^2$ and about 100 mm$^2$, or between about 0.1 mm$^2$ and about 10 mm$^2$. For example, the mesh may be comprised of squares, such that each square is 1 mm×1 mm, with an area of 1 mm$^2$.

The mesh may be imbedded into the wall of the devices, and is thinner than the thickness of the wall. The mesh may be positioned generally within the middle of the wall or may be closer to one side of the wall. The mesh may be surrounded by the wall material, which allows the wall surface of the devices to be smooth.

The surfaces of the devices may comprise a protective polymeric coating. One suitable type of polymer is parylene. Parylene is the name for a series of polymers based on the monomer, para-xylene (p-xylene), or 1,4 dimethyl-benzene. There are three commercially available variations of parylene that display differences at the monomeric level: parylene N, parylene C, and parylene D. In one preferred embodiment, the instant invention uses parylene N or parylene C. Parylene is applied in a thickness of about 0.00003" to 0.0001" and more preferably in a thickness of about 0.00005".

The backbone of the parylene polymer is made entirely of carbon and thereby is not vulnerable to hydrolytic breakdown in an aqueous environment. Parylene also has excellent properties as a film lubricant and its coefficient of friction approaches TEFLON®. Also, with a dielectric constant relatively independent of frequency and temperature, parylene also is an excellent electric insulator.

The devices contemplated by the present invention can be formed using any number of materials conventional to those skilled in the art for airway management devices. For example, one preferable material is medical or implant grade silicone but other materials such as polyvinylchloride (PVC) could also be used without departing from the scope of the present invention.

Figure 2:
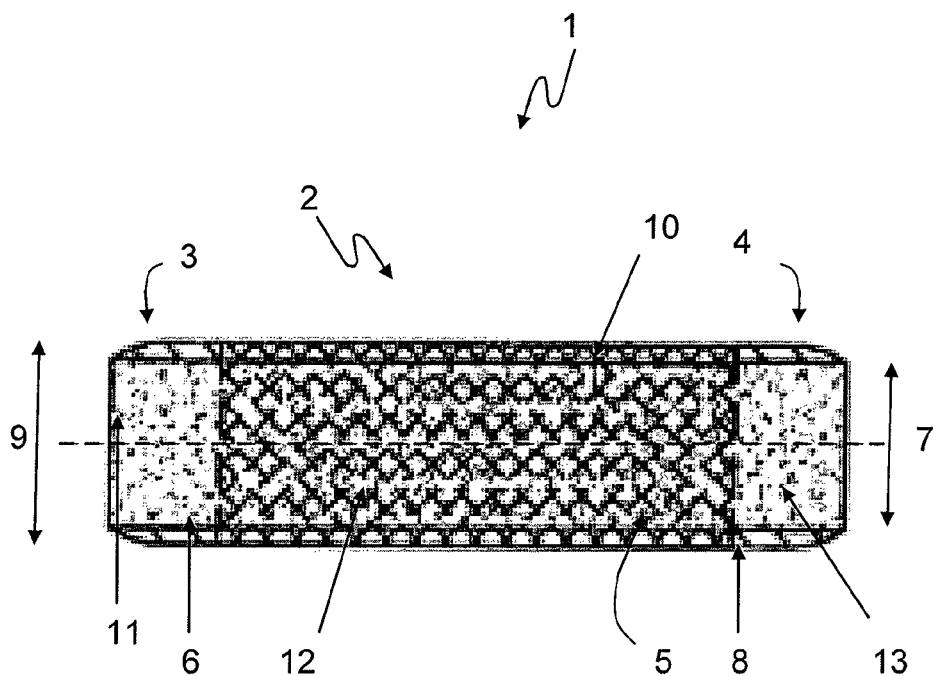
FIG. 2 is a cut-away view of an airway management device according to one aspect of the present invention.
Figure 2:
Figure 2:

One aspect of the present invention relates to an airway management device 1 comprising a fiber mesh imbedded into one or more portions of its walls. Embodiments of the present invention are depicted in FIGS. 1-19. For example, FIGS. 1 and 2 show an airway management device which may comprise a first tubular arm 2 comprising a first open end 3, a second open end 4, a lumen 5 extending therethrough having an inner surface 6 and an inner circumference 7, an outer surface 8, an outer circumference 9, a tubular wall 10 between the inner surface and outer surface, a longitudinal axis 11 through the center of the lumen 4 of the first tubular arm 2, and a fiber mesh 12 as described above which are imbedded in one or more portions of the tubular wall 10.

The mesh 12 may be imbedded in tubular wall 10 in various location throughout the first tubular arm 1 in various patterns or randomly. For example, the mesh 12 may be imbedded in bands around the first tubular arm 2, in rows extending along the length of the first tubular arm 2, or a combination thereof. The mesh 12 may also be imbedded in the tubular wall 10 in bands circling the first tubular arm 2 at the first open end 3 and the second open end 4, or may be in the middle between these ends. Further, the mesh 12 may be imbedded in the tubular walls 10 throughout the entire first tubular arm 2.

Figure 3:
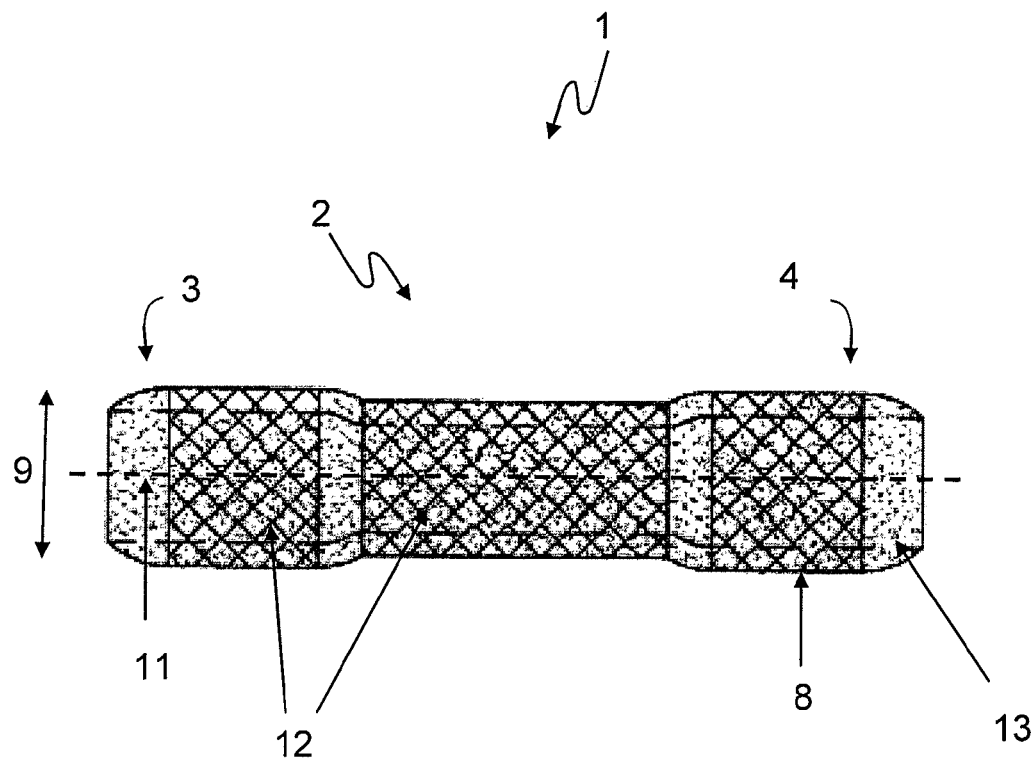
FIG. 3 is a side view of an airway management device comprising a varying outer circumference according to one aspect of the present invention.
Figure 3:
Figure 3:
Figure 4:
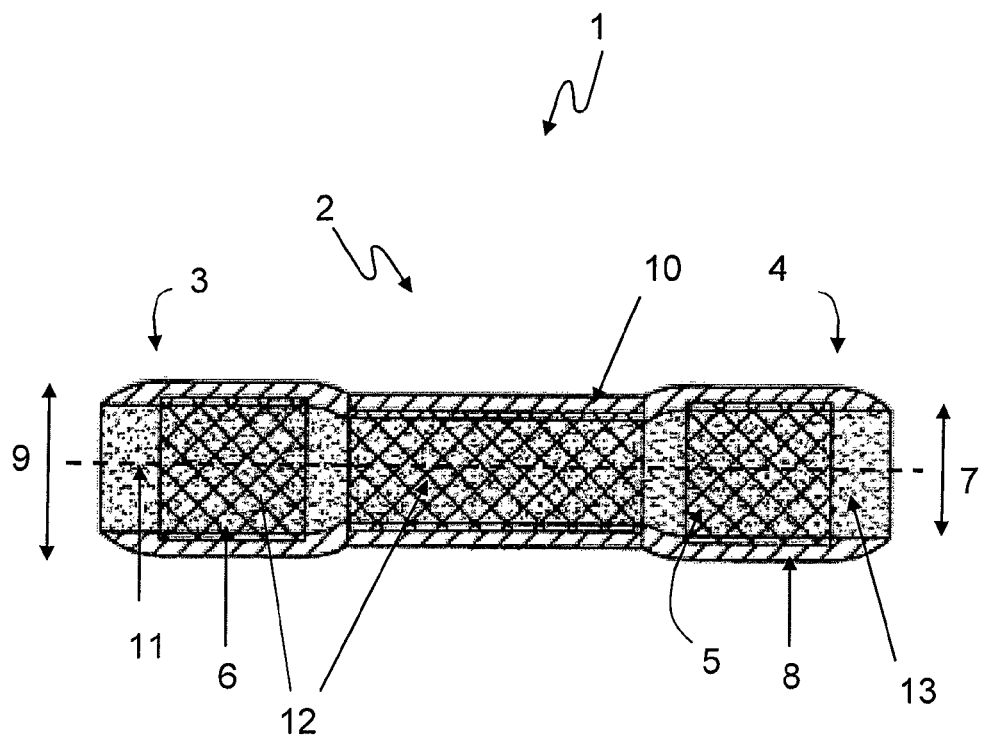
FIG. 4 is a cut-away side view of an airway management device comprising a varying outer circumference according to one aspect of the present invention.
Figure 5:
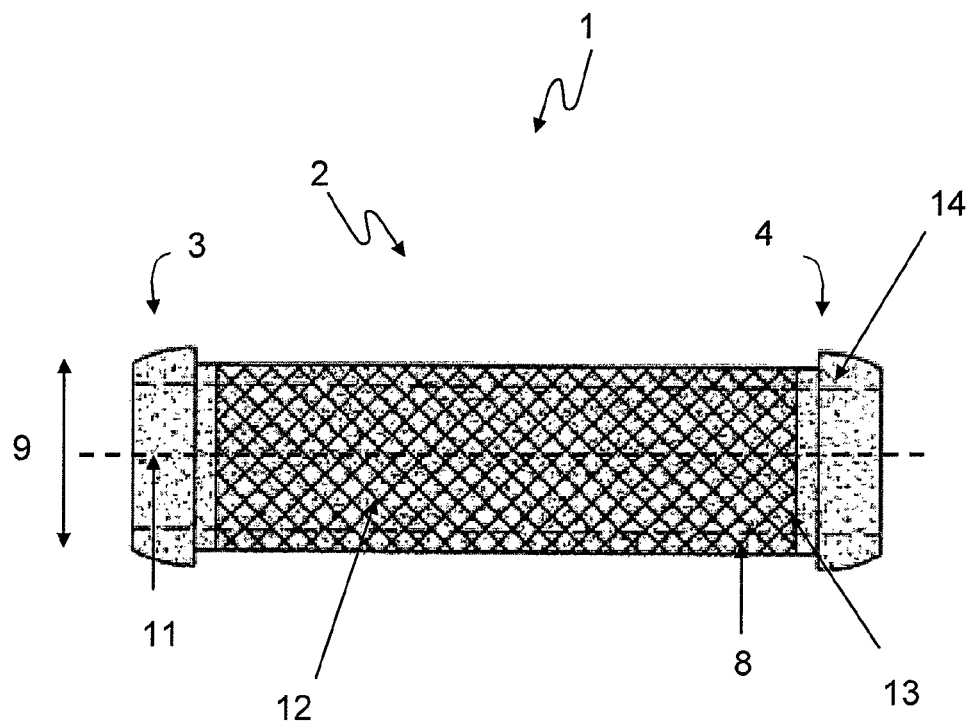
FIG. 5 is a side view of an airway management device comprising rings according to one aspect of the present invention.
Figure 5:
Figure 5:
Figure 6:
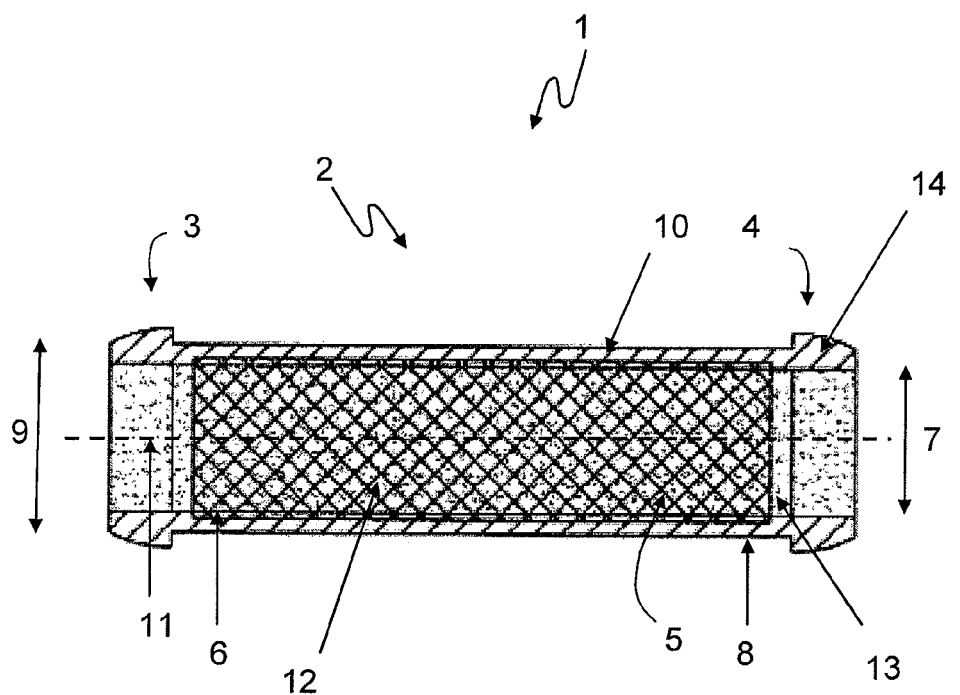
FIG. 6 is a cut-away side view of an airway management device comprising rings according to one aspect of the present invention.
Figure 6:
Figure 6:
Figure 7:
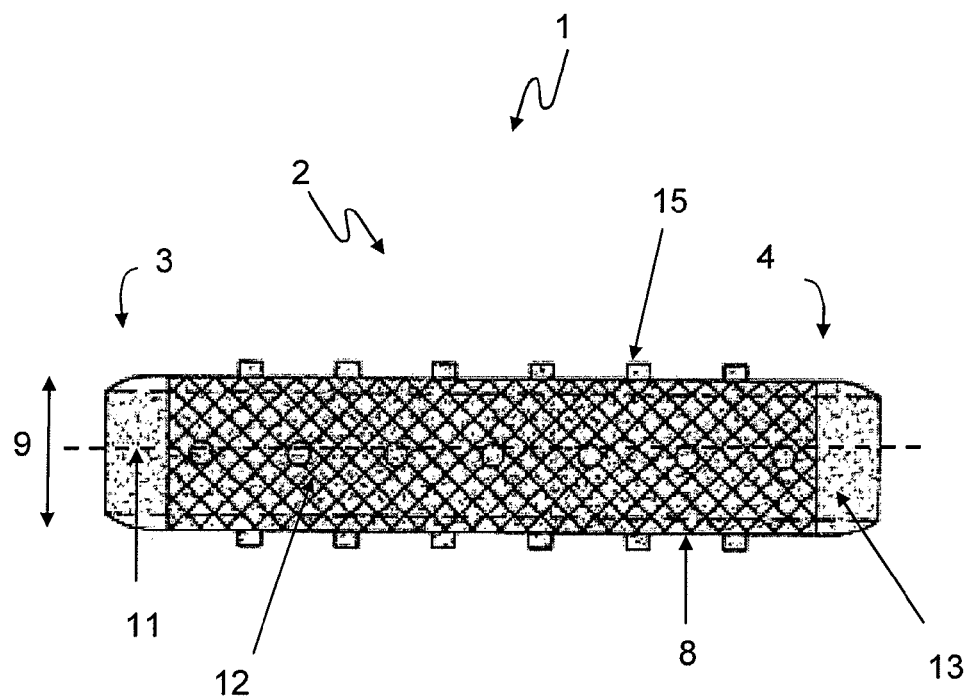
FIG. 7 is a side view of an airway management device comprising posts according to one aspect of the present invention.
Figure 7:
Figure 7:
Figure 8:
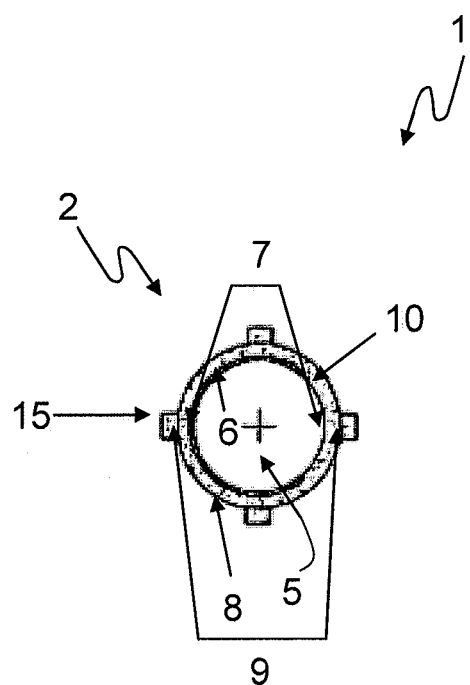
FIG. 8 is an end view of an airway management device comprising posts according to one aspect of the present invention.
Figure 8:
Figure 8:
Figure 9:
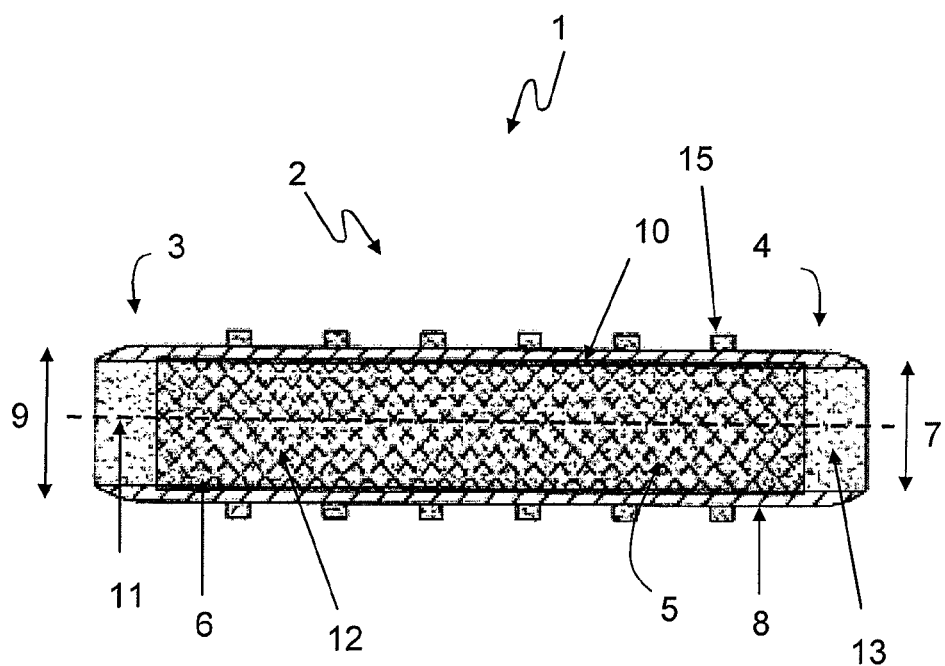
FIG. 9 is a cut-away side view of an airway management device comprising posts according to one aspect of the present invention.
Figure 10:
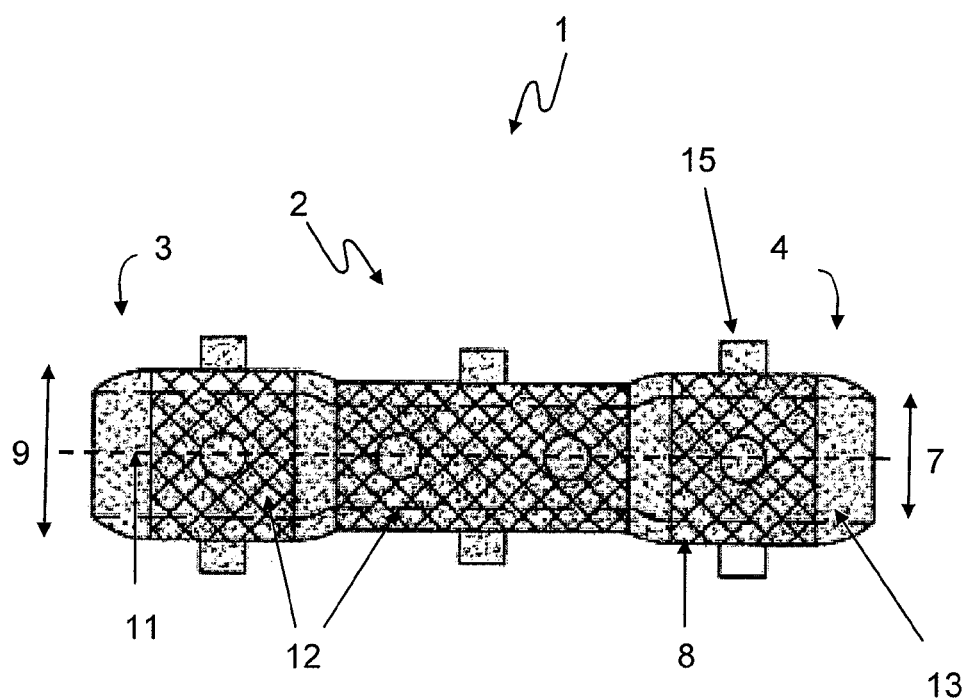
FIG. 10 is a side view of an airway management device comprising a varying outer circumference and comprising posts according to one aspect of the present invention.
Figure 11:
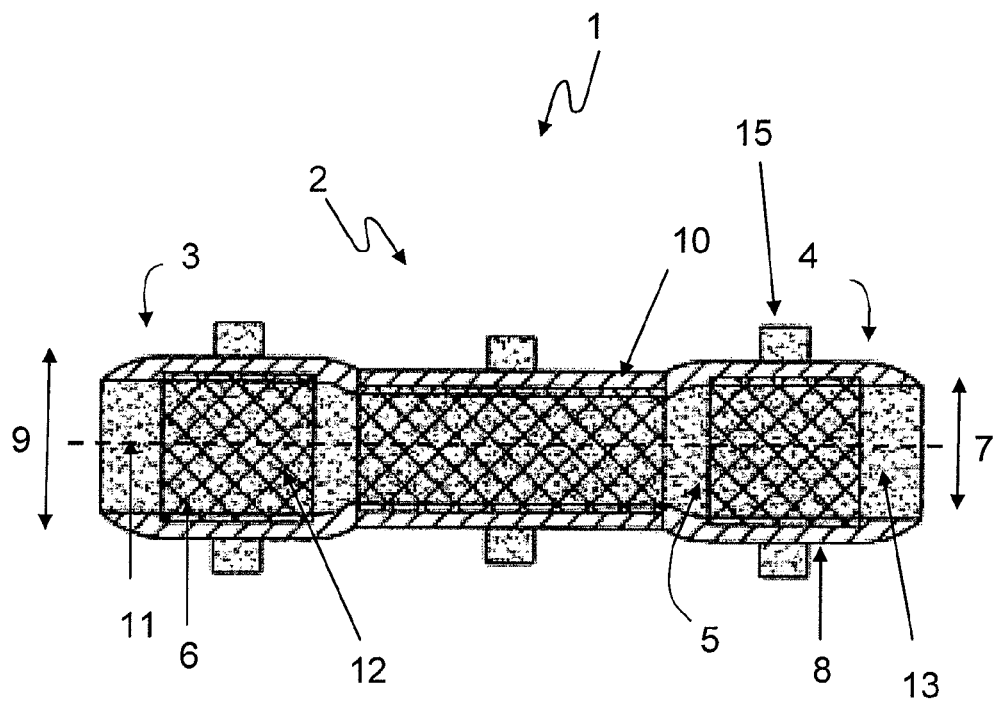
FIG. 11 is a cut-away side view of an airway management device comprising a varying outer circumference and comprising posts according to one aspect of the present invention.
Figure 11:
Figure 11:

The length of the first tubular arm 2, the inner circumference 7, and the outer circumference 9 may be chosen by one of ordinary skill in the art in consideration of the purpose, e.g., bronchial stent, tracheal stent, etc., for which the device is used. The inner outer circumference 9 and the inner circumference 7 may be constant throughout the length of the first tubular arm 2, or the outer circumference 9 and the inner circumference 7 may vary throughout the length of the first tubular arm 2. For instance, FIGS. 3 and 4 depict an embodiment such that the outer circumference 9 is greater in the regions near first open end 3 and second open end 4 than the region between, which results in a first tubular arm 2 comprising an "hourglass" shape. On the other hand, the first tubular arm 2 may comprise an "inverted hourglass shape" if the outer circumference 9 is smaller in the regions near first open end 3 and second open end 4 than the region therebetween. The inner circumference 7 may also similarly vary along the length of the first tubular arm 2.

The first tubular arm 2 may further comprise a protective coating 13 on one or more portions of the inner surface, one or more portions on the outer surface, or a combination thereof. As described above, the protective coating may be a polymeric coating, such as a parylene coating.

The first tubular arm 2 may further comprise a means to prevent movement or displacement of the airway management device 1 during use. Means to prevent movement or displacement may comprise one or more rings 14 around the outer circumference 9 of the first tubular arm 2, one or more posts or protrusions 15 that extend from the outer surface 8 of the device, or the like. For example, the embodiments depicted in FIGS. 5 and 6 demonstrate an airway management device 1 comprising a first tubular arm 2, which comprises rings 14 as a means to prevent movement or displacement of the device. The dimensions of the rings 14 can be determined by one skilled in the art in consideration of its use airways.

The rings 14 may be located at the first open end 3, the second open end 4, any site therebetween, or any combination thereof. In the embodiment shown in FIGS. 5 and 6, the rings 14 are located at the first open end 3 and the second open end 4. The rings may also comprise a protective coating 13 as described above.

Another example of means to prevent displacement or movement of the airway management device 1 may be posts 15, or protrusions, which extend radially from the surface 8 of the first tubular arm 2. For instance, FIGS. 7-11 depict an airway management device 1 comprising a first tubular arm 1, wherein the tubular arm 1 comprises posts 15. The posts 15 can be of any shape or form, including cubic posts, cylindrical posts, pyramidal posts, and other prism-shaped posts. The dimensions of the posts 15 can be determined by one skilled in the art in view of its use in airways.

The posts may be distributed evenly or unevenly around the circumference of the first tubular arm 2, and there may be one or more rows of posts 15. In the embodiments depicted in FIGS. 7-11, the posts are in four rows distributed evenly around the outer circumference 9 of the first tubular arm 2. The posts may also comprise a protective coating 13 as described above.

Figure 12:
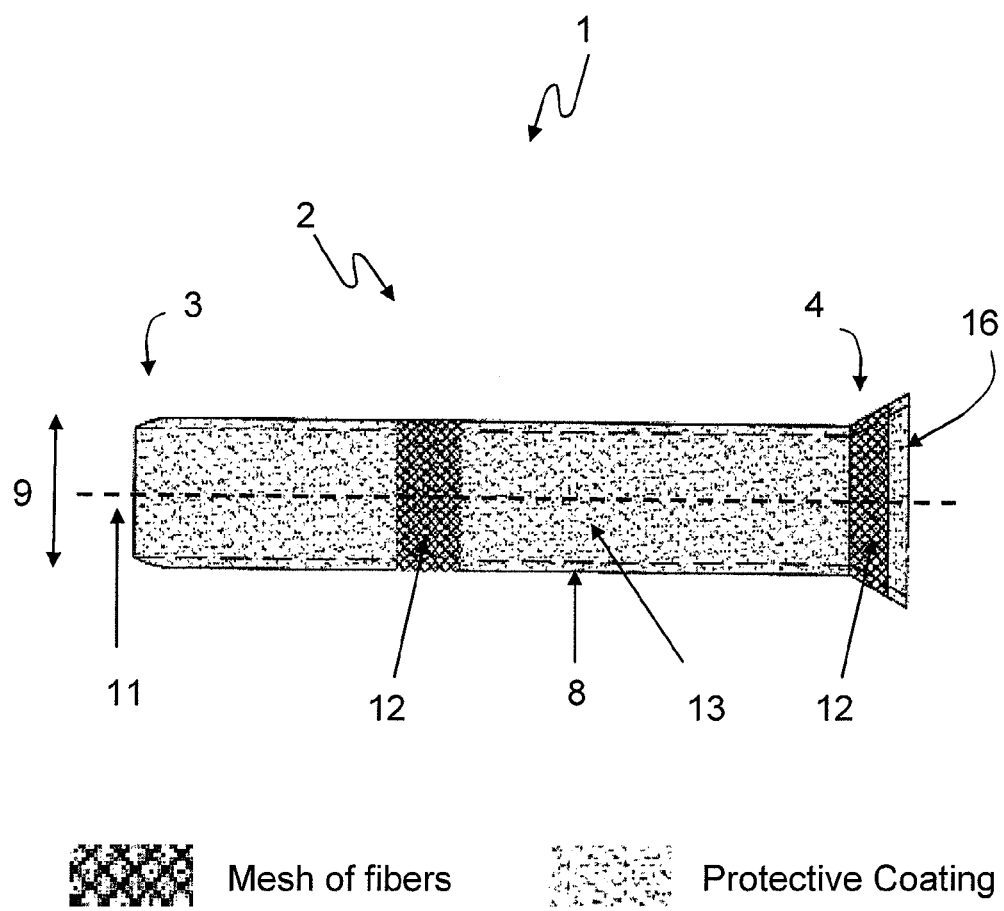
FIG. 12 is a side view of an esophageal management device comprising a funnel according to one aspect of the present invention.
Figure 12:
Figure 12:
Figure 13:
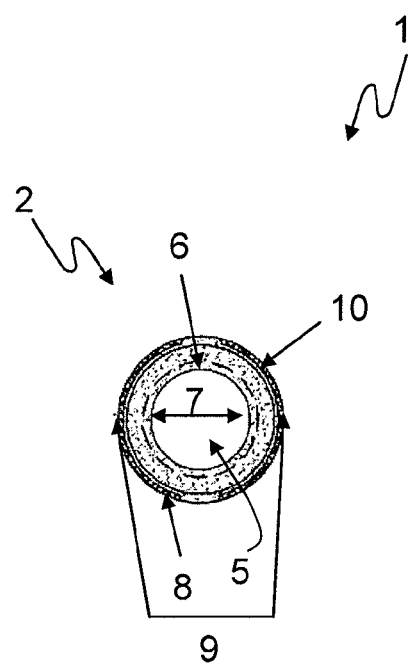
FIG. 13 is an end view of an esophageal management device comprising a funnel according to one aspect of the present invention.
Figure 13:
Figure 13:
Figure 14:
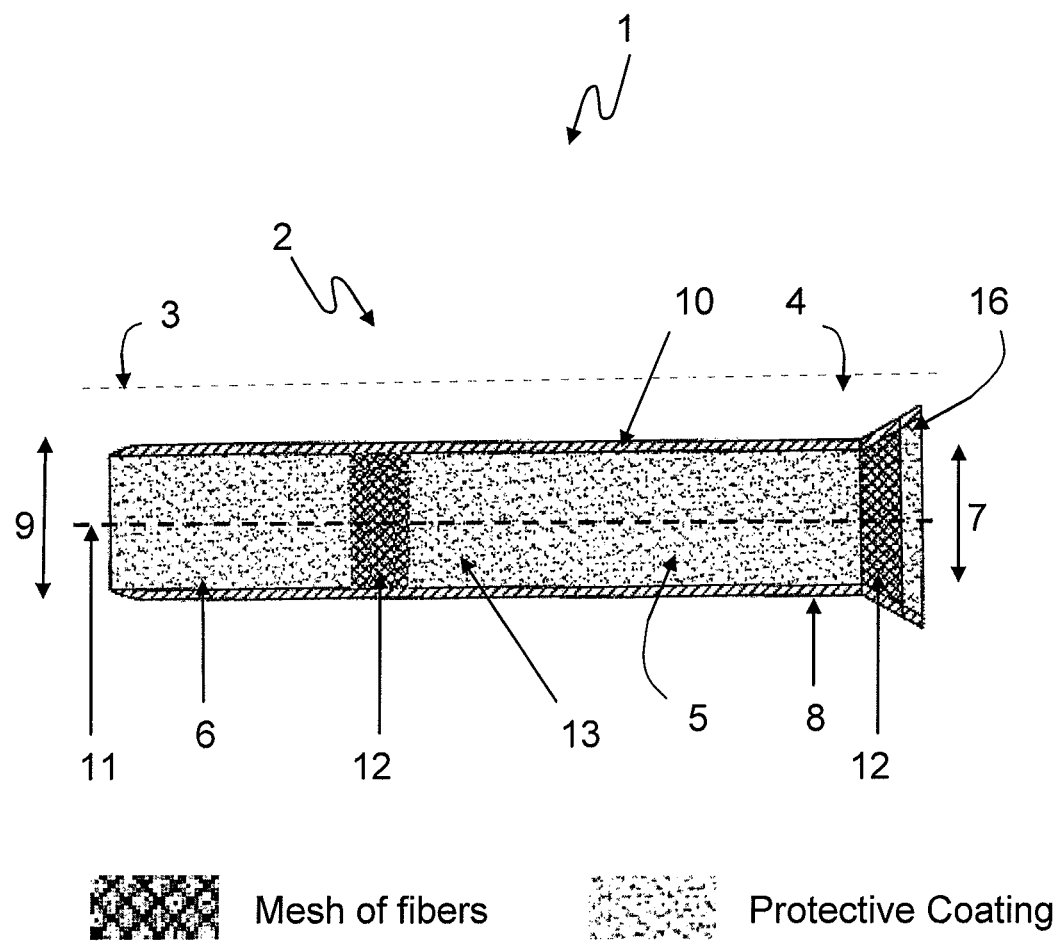
FIG. 14 is a cut-away side view of an esophageal management device comprising a funnel according to one aspect of the present invention.

The esophageal management device 1 may also comprise a first tubular arm 2 comprising a funnel 16, as shown in FIGS. 12-14. The funnel 16 may be on the first open end 3, the second open end 4, or both. The mesh 12 may be imbedded in a portion of the funnel 16, such as around the circumference of the funnel 16. For example, the mesh 12 may be imbedded adjacent to the edge of the funnel 16 or may be adjacent to the where the funnel 16 meets the open end of the first tubular arm 2. Alternatively, the mesh 12 may be imbedded in the first tubular arm 2 at an end or in the middle, distributed throughout, in a single portion, or in multiple portions. Further, the inner surface 17 of the funnel 16 and/or the outer surface 18 of the funnel 16 may comprise a protective coating 13.

Figure 15:
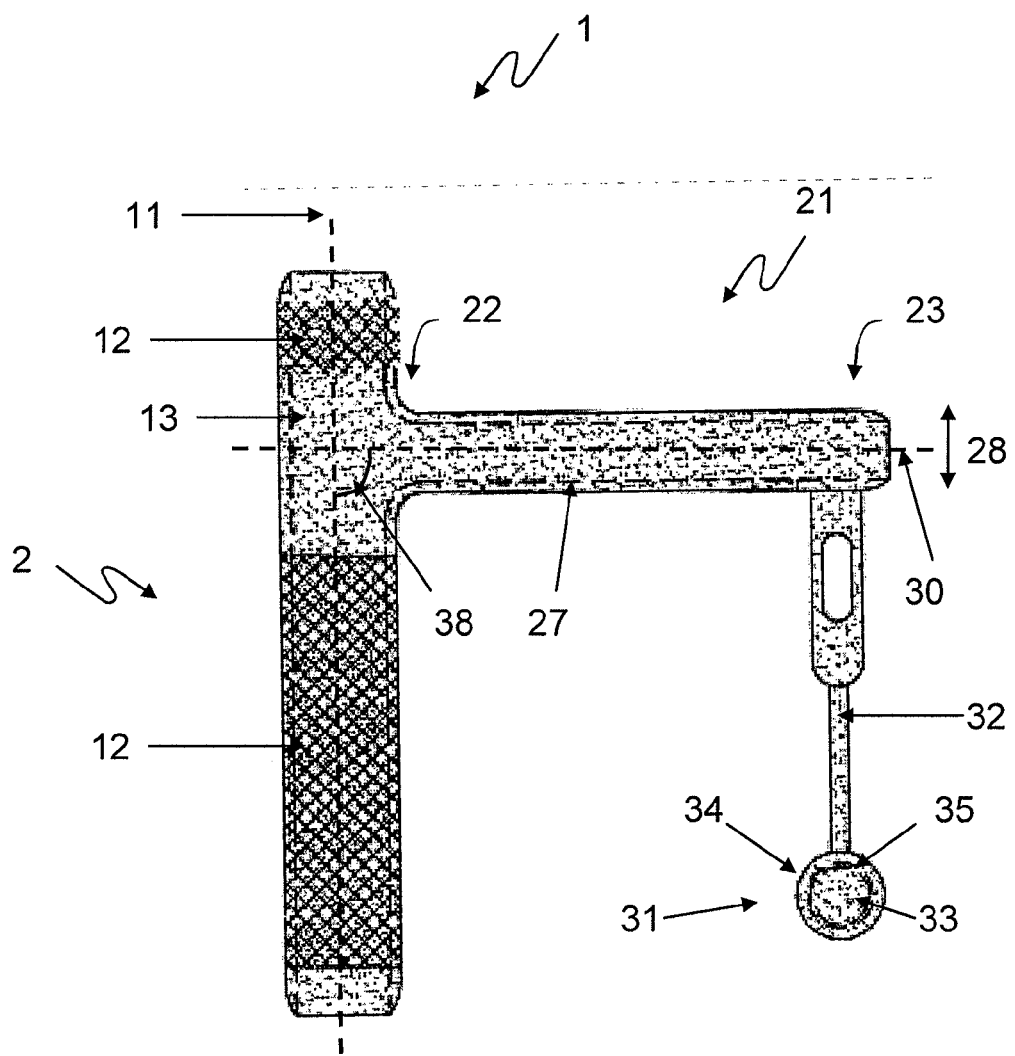
FIG. 15 is a side view of an airway management device comprising a second tubular arm according to one aspect of the present invention.
Figure 16:
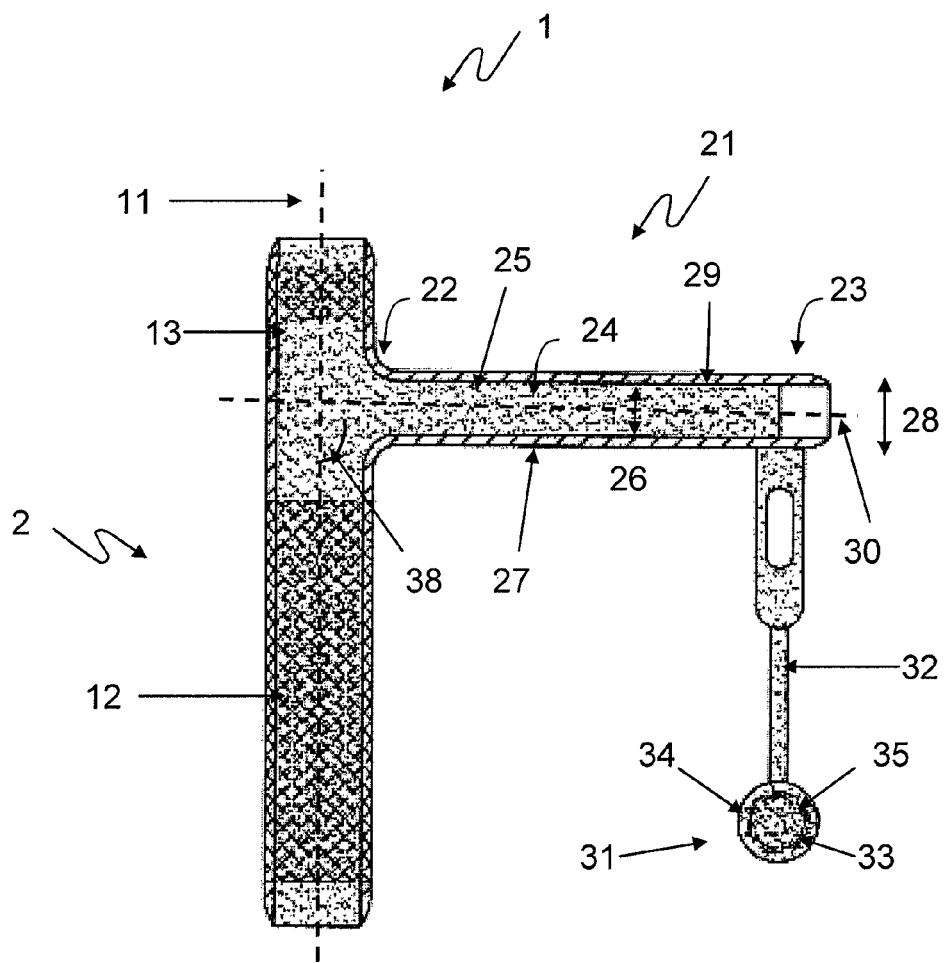
FIG. 16 is a cut-away side view of an airway management device comprising a second tubular arm according to one aspect of the present invention.

The airway management device 1 may comprise a first tubular arm 2, and may further comprise a second tubular arm 21, as shown in FIGS. 15 and 16. The second tubular arm 21 may comprise a first open end 22, a second open end 23, a lumen 24 extending therethrough having an inner surface 25 and an inner circumference 26, an outer surface 27, an outer circumference 28, a tubular wall 29 between the inner surface 25 and outer surface 27, and a longitudinal axis 30 through the center of the lumen 24 of the second tubular arm 21. The second tubular arm 21 may be connected to the first tubular arm 2 through the first open end 22 to between the first open end 3 and the second open end 4 of the first tubular arm 2. The lumen 5 of the first tubular arm 2 and the lumen 24 of the second tubular arm 21 may be continuous.

The first tubular arm 2 may comprise a mesh 12 of fibers imbedded in one or more portions of the tubular wall. For instance, the mesh 12 may be imbedded in the first tubular arm 2 in regions on either or both sides of the connection between the second tubular arm 21 and the first tubular arm 2 (see FIGS. 15 and 16). The second tubular arm 21 may comprise a mesh 12 of fibers imbedded in one or more portions of the tubular wall 29, as described above. The second tubular arm 21 may also comprise a protective coating 13 on one or more portions of the inner surface 25, one or more portions on the outer surface 27, or a combination thereof.

Moreover, the second tubular arm 21 may comprise a means to prevent movement or displacement as described above.

Furthermore, the second tubular arm 21 may comprise a plug 31 that inserts into the second open end 23 of the second tubular arm 21. A tether 32 may be attached to the second tubular arm 21 and may connect the plug 31 to the second tubular arm 21. The plug 31 may have a cylindrical wall 33 attached axially to a base 34 with a tapered outer wall 35, as shown in FIGS. 15 and 16. The tapered outer wall 35 may have a first proximal portion (not shown) and a second distal portion (not shown) to the base. The plug 31 may be of a dimension and configuration to fit tightly adjacent to the inner surface of the second open end 23 of the second tubular arm 21. The second portion of the outer wall 33 of plug 31 may or may not be coated.

The longitudinal axis 11 of the first tubular arm 2 may form an angle 36 with the longitudinal axis 30 of the second tubular arm 21. The angle 36 may be between 0° and 180°, may be between about 45° and 135°, or may be about 90°.

Figure 17:
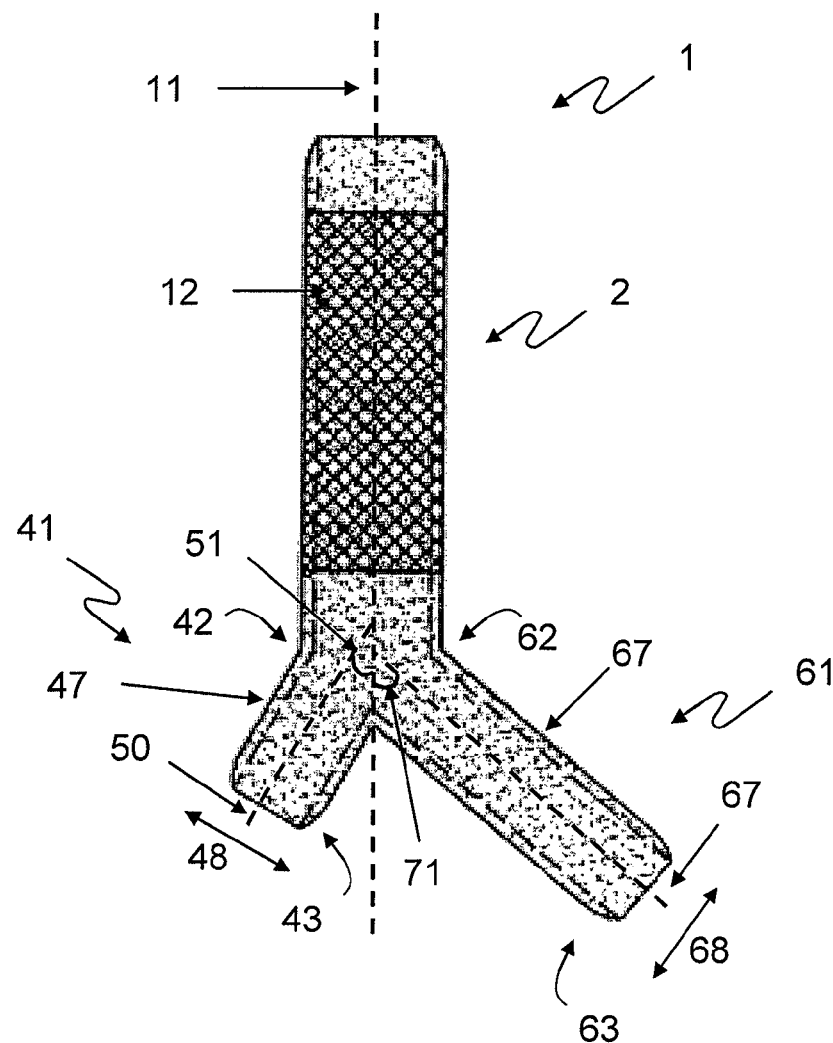
FIG. 17 is a side view of an airway management device comprising a bifurcation comprising a first tubular diagonal arm and a second tubular diagonal arm according to one aspect of the present invention.
Figure 18:
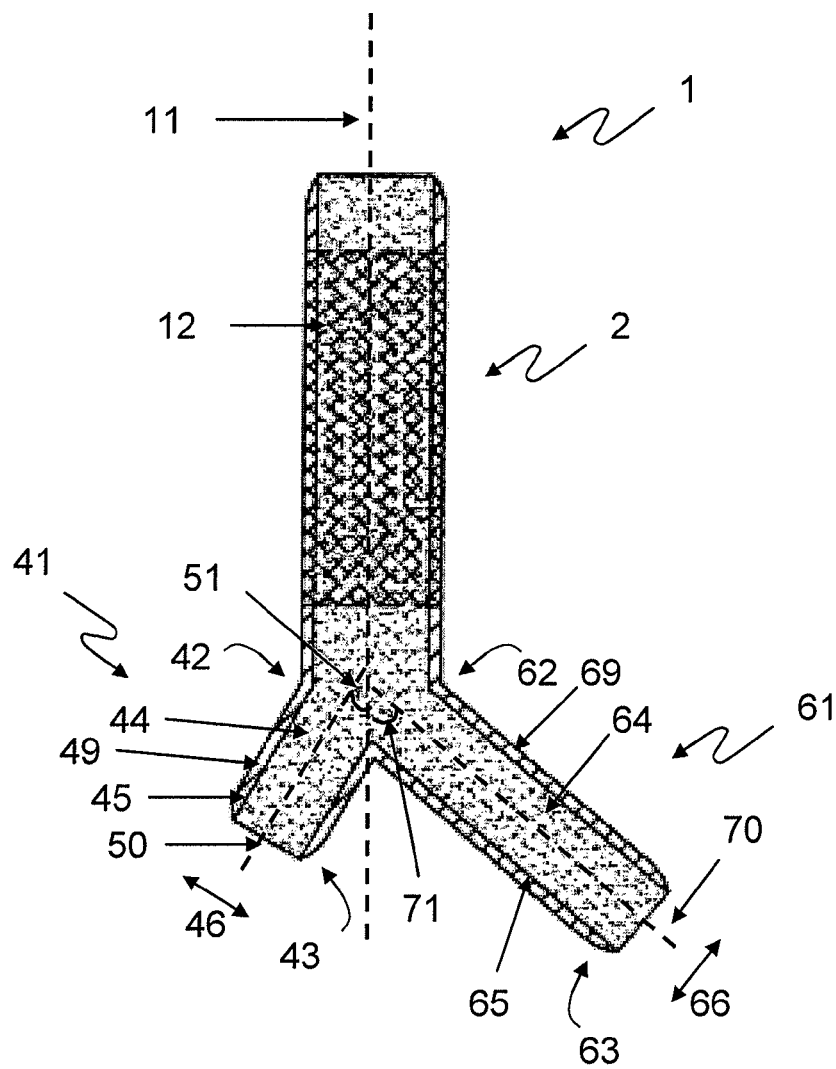
FIG. 18 is a cut-away side view of an airway management device comprising a bifurcation comprising a first tubular diagonal arm and a second tubular diagonal arm according to one aspect of the present invention.

The airway management device 1 may comprise a first tubular arm 2 comprising a bifurcation on the second open end, such that the second open end bifurcates into a first tubular diagonal arm 41 and a second tubular diagonal arm 61, as shown in FIGS. 17 and 18. The first tubular diagonal arm 41 may comprise a first open end 42, a second open end 43, a lumen 44 extending therethrough having an inner surface 45 and an inner circumference 46, an outer surface 47, an outer circumference 48, a tubular wall 49 between the inner surface 45 and outer surface 47, and a longitudinal axis 50 through the center of the lumen 44 of the first diagonal arm 41. The second tubular diagonal arm 61 may comprise a first open end 62, a second open end 63, a lumen 64 extending therethrough having an inner surface 65 and an inner circumference 66, an outer surface 67, an outer circumference 68, a tubular wall 69 between the inner surface 65 and outer surface 67, and a longitudinal axis 70 through the center of the lumen 64 of the first diagonal arm 61. The lumen 44 of the first tubular diagonal arm 41 and the lumen 64 of the second tubular diagonal arm 51 may be continuous with the lumen 5 of the first tubular arm 2.

The lengths of the first tubular diagonal arm 41 and the second tubular diagonal arm 61 may or may not be equal. The dimensions of the first tubular diagonal arm 41 and the second tubular diagonal arm 61 can be determined by one skilled in the art based on their applications and use in airways.

The first tubular diagonal arm 41 and the second tubular diagonal arm 61 may also comprise a fiber mesh 12 imbedded in one or more portions of their respective tubular walls (49 and 69). The first tubular diagonal arm 41 and the second tubular diagonal arm 61 may further comprise a protective coating 13 on one or more portions of their respective inner surfaces (45 and 65) and outer surfaces (47 and 67).

Further, the first tubular diagonal arm 41 and/or the second tubular diagonal arm 61 may comprise a means to prevent movement or displacement as described above.

The longitudinal axis 11 of the first tubular diagonal arm 2 may form a first angle 51 with the longitudinal axis 50 of the first diagonal arm 41. The longitudinal axis 11 of the first tubular diagonal arm 2 may also form a second angle 71 with the longitudinal axis 60 of the second diagonal arm 61. Each of the first angle 51 and the second angle 71 may be between 0° and 180°, may be between about 45° and 135°, or may be about 90°. The first angle 51 and the second angle 71 may or may not be equal.

Referring to the location of the first tubular diagonal arm 41 and the second tubular diagonal arm 61 around the outer circumference 9 of the first tubular arm 2, the first tubular diagonal arm 41 and the second tubular diagonal arm 61 may be 180° apart around the circumference. In some embodiments, the first tubular diagonal arm 41 and the second tubular diagonal arm 61 may be between 0° and 180°, or between 45° and 135° or about 90° apart around the circumference.

Figure 19:
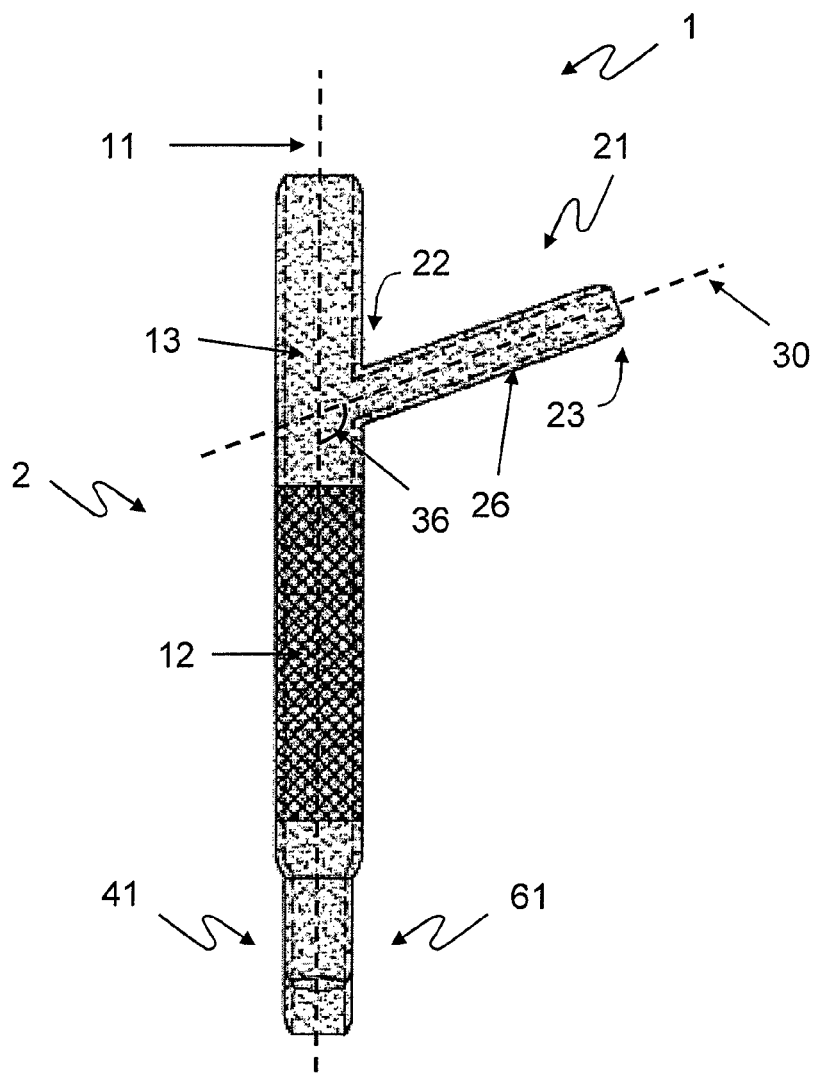
FIG. 19 is a side view of an airway management device comprising a second tubular arm, and comprising a bifurcation comprising a first tubular diagonal arm and a second tubular diagonal arm according to one aspect of the present invention.
Figure 20:
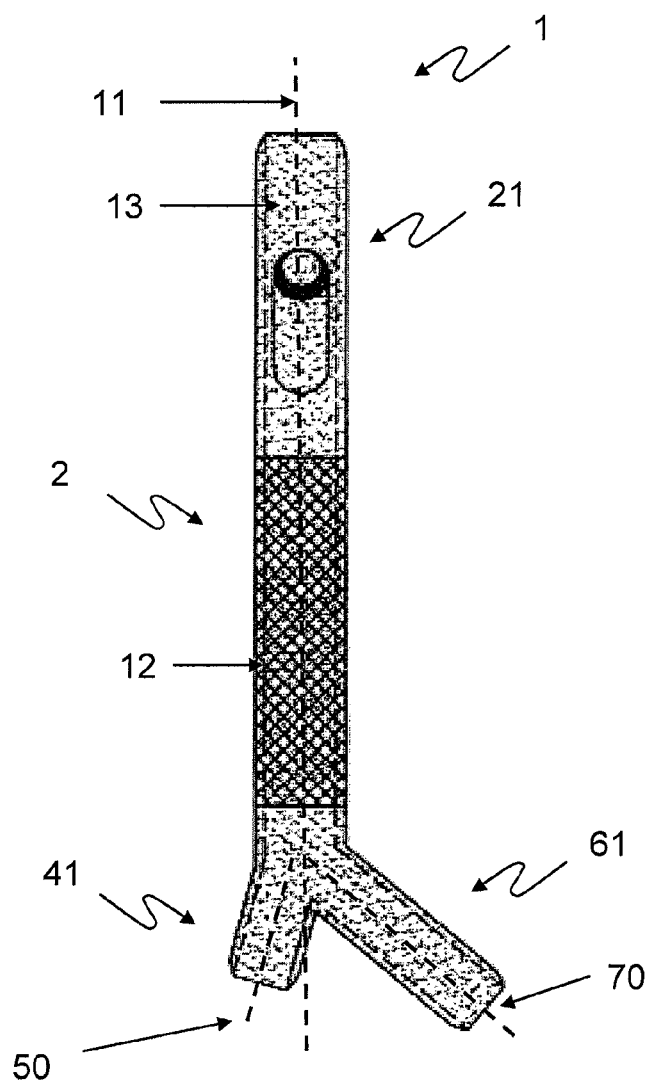
FIG. 20 is a second side view of an airway management device comprising a second tubular arm, and comprising a bifurcation comprising a first tubular diagonal arm and a second tubular diagonal arm according to one aspect of the present invention.
Figure 21:
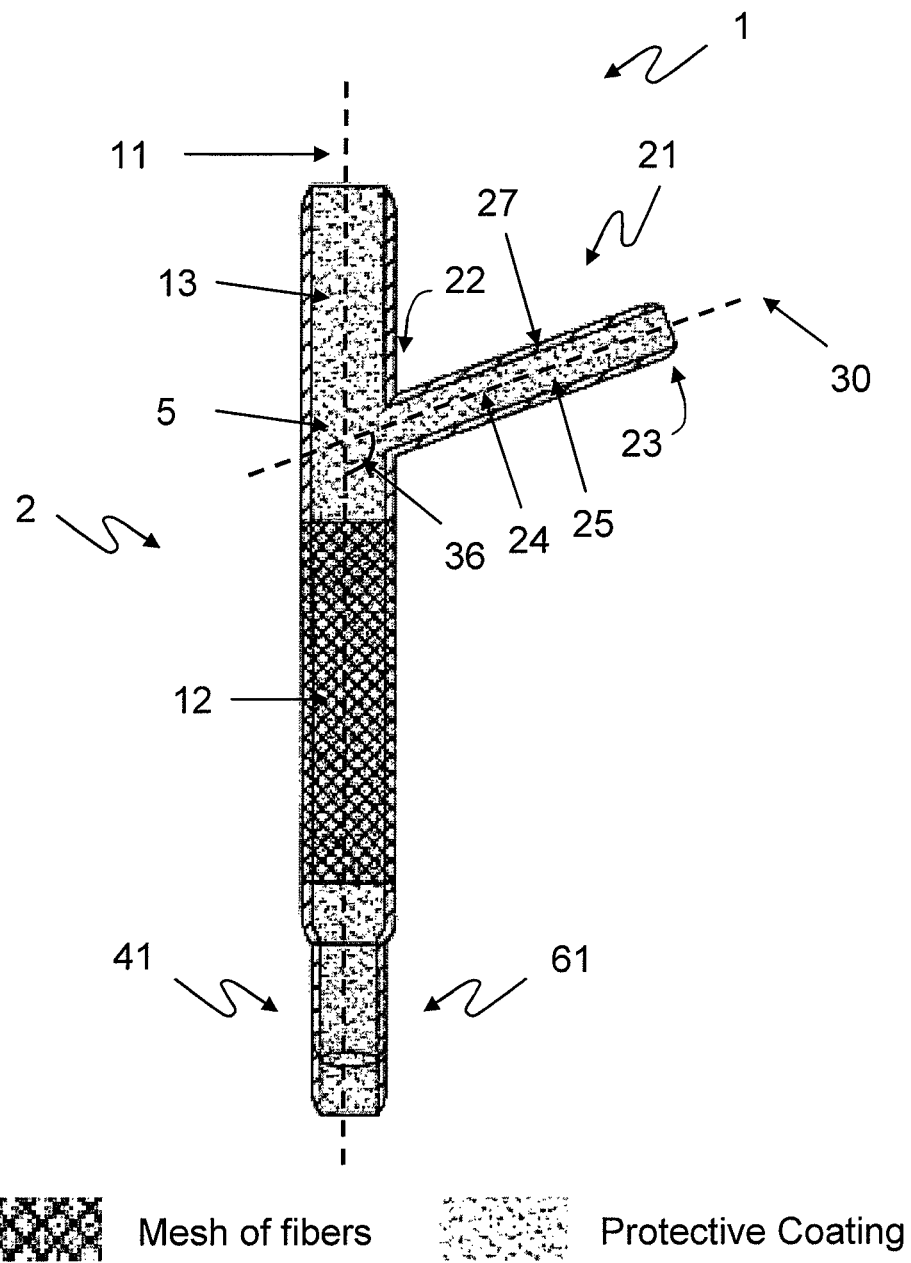
FIG. 21 is a cut-away second side view of an airway management device comprising a second tubular arm, and comprising a bifurcation comprising a first tubular diagonal arm and a second tubular diagonal arm according to one aspect of the present invention.

The airway management device 1 comprising a first tubular arm 2, which comprises a second open end that bifurcates into a first tubular diagonal arm 41 and a second tubular diagonal arm 61, may further comprise a second tubular aim 21 which extends from the first tubular arm 2, as shown in FIGS. 19-21. The second tubular arm 21, as described above, may comprise a first open end 22, a second open end 23, a lumen 24 extending therethrough having an inner surface 25 and an inner circumference (not shown), an outer surface 26, an outer circumference (not shown), a tubular wall 27 between the inner surface 25 and outer surface 26, and a longitudinal axis 30 through the center of the lumen 24 of the second tubular arm 21. The second tubular arm 21 is connected to the first tubular arm 2 through the first open end 22 to the first tubular arm 2. The lumen 5 of the first tubular arm 2 and the lumen 24 of the second tubular arm 21 may be continuous.

A fiber mesh 12 may be imbedded in one or more portions of the first tubular arm 2, the second tubular arm 21, the first tubular diagonal arm 41, or the second tubular diagonal arm 61. For example, the second tubular arm 21 may comprise a fiber mesh 12 imbedded in one or more portions of the tubular wall 29, as described above.

The second tubular arm 21 may also comprise a protective coating 13 on one or more portions of the inner surface 25, one or more portions on the outer surface 27, or a combination thereof.

The longitudinal axis 11 of the first tubular arm 2 may form an angle 36 with the longitudinal axis 30 of the second tubular arm 21. The angle 36 may be between 0° and 180°, may be between about 45° and 135°, or may be about 90°.

Referring to the location of the second tubular arm 21, the first tubular diagonal arm 41, and the second tubular diagonal arm 61 around the outer circumference 9 of the first tubular arm 2, the second tubular arm 21 may be aligned with either of the tubular diagonal arms 21 or 41, or may be unaligned with either tubular diagonal arm 21 or 41 and may be between 0° and 180° apart around the circumference from either tubular diagonal arm 21 or 41. If there is more than one tubular arm extending from the first tubular arm 2, these additional arms may aligned or unaligned with the tubular diagonal arms 21 and 41. Further, these addition arms may at the same site along the length of the tubular arm 2 or they may be at different sites.

Therefore, FIGS. 1-21 depict various embodiments of the airway or esophageal management device. For example, the embodiments shown in FIGS. 1-11 may be used as a bronchial or tracheal stent, while the embodiments of FIGS. 12-14 may be used as a salivary bypass tube. The embodiments of FIGS. 15 and 16 may be used as a T-tube, and the embodiments of FIGS. 17 and 18 may be used as a Y-stent. Finally, the embodiments of FIGS. 19-21 may be used as a TY-tube.

Figure 22:
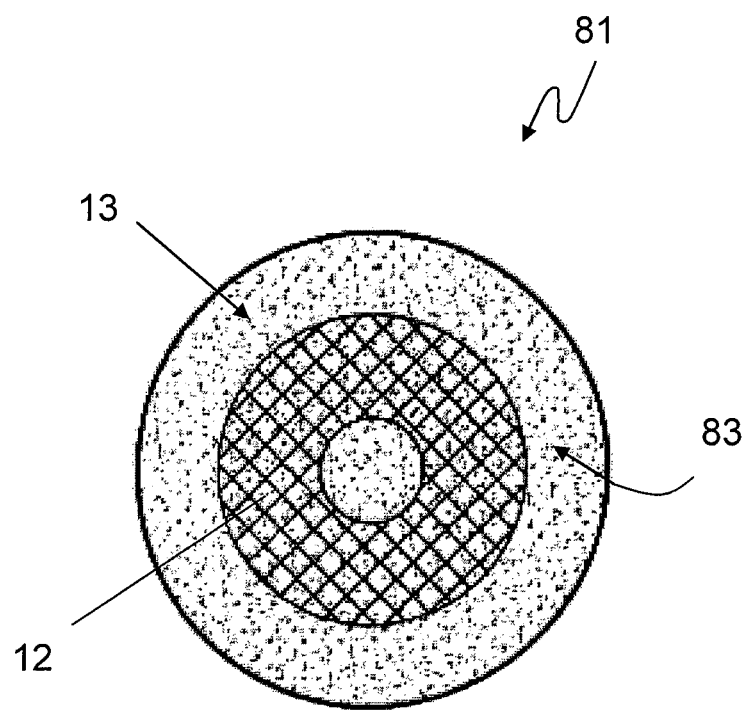
FIG. 22 is a top view of a nasal septal button according to one aspect of the present invention.
Figure 22:
Figure 22:
Figure 23:
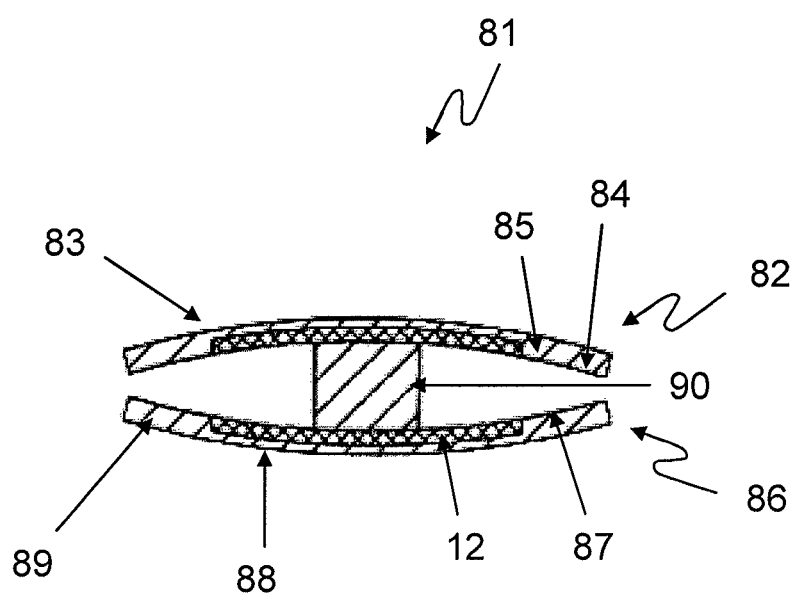
FIG. 23 is a cut-away side view of a nasal septal button according to one aspect of the present invention.
Figure 23:
Figure 24:
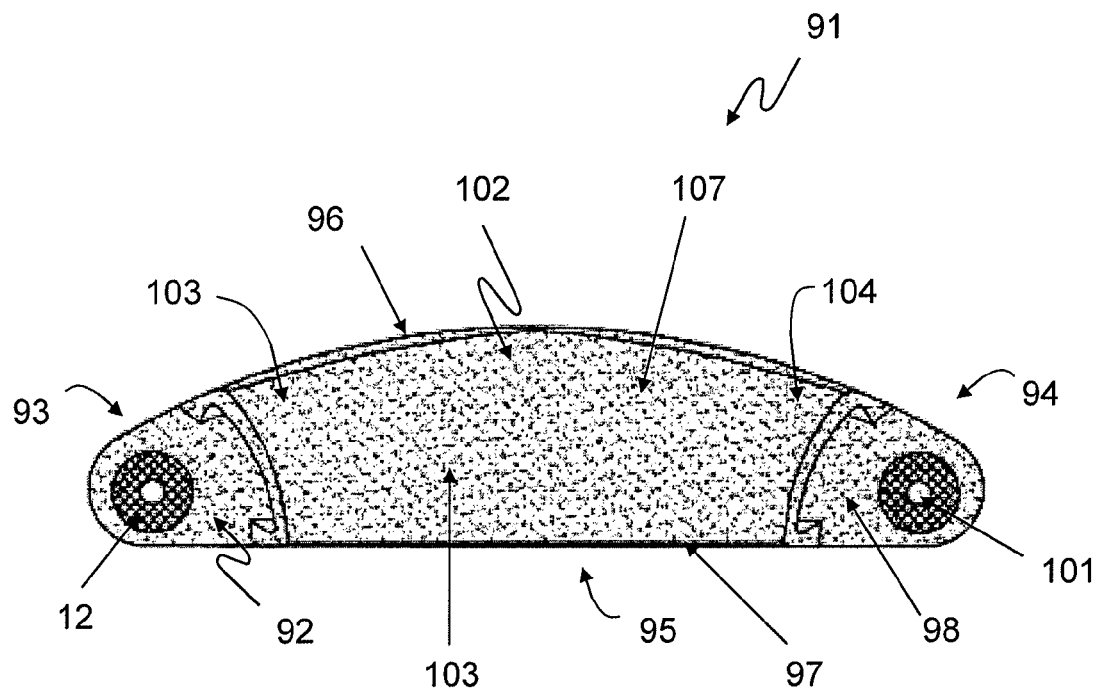
FIG. 24 is a side view of a Tellez Nasal Splint according to one aspect of the present invention.
Figure 24:
Figure 24:
Figure 25:
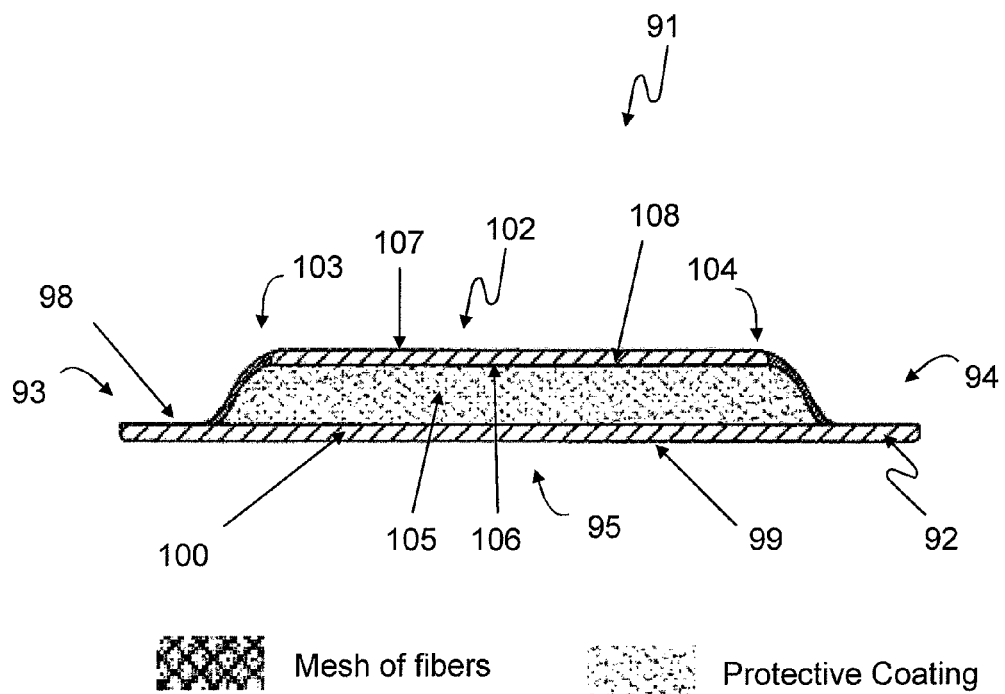
FIG. 25 is a cut-away bottom view of a Tellez Nasal Splint according to one aspect of the present invention.
Figure 26:
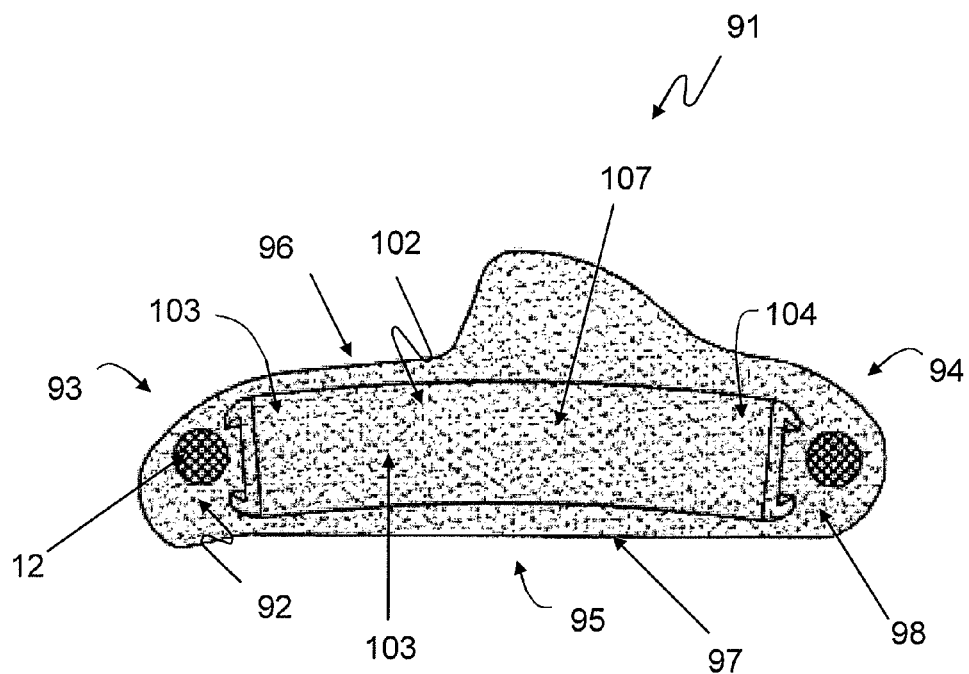
FIG. 26 is a side view of a Doyle Shark Nasal Splint according to one aspect of the present invention.
Figure 26:
Figure 26:
Figure 27:
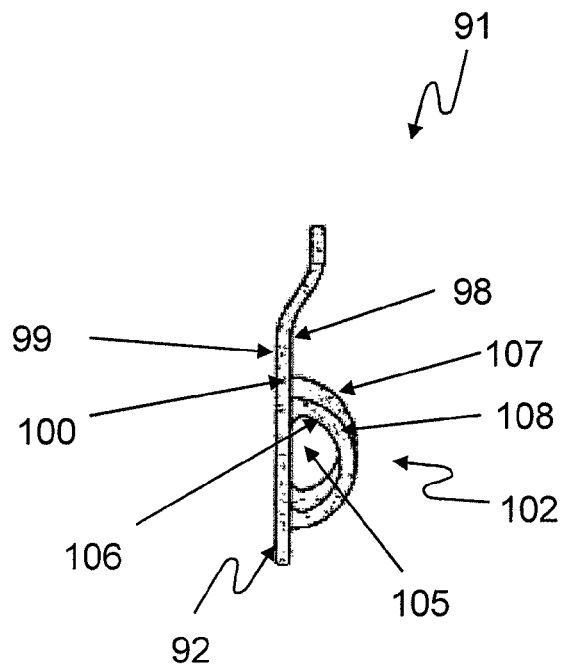
FIG. 27 is an end view of a Doyle Shark Nasal Splint according to one aspect of the present invention.
Figure 27:
Figure 27:
Figure 28:
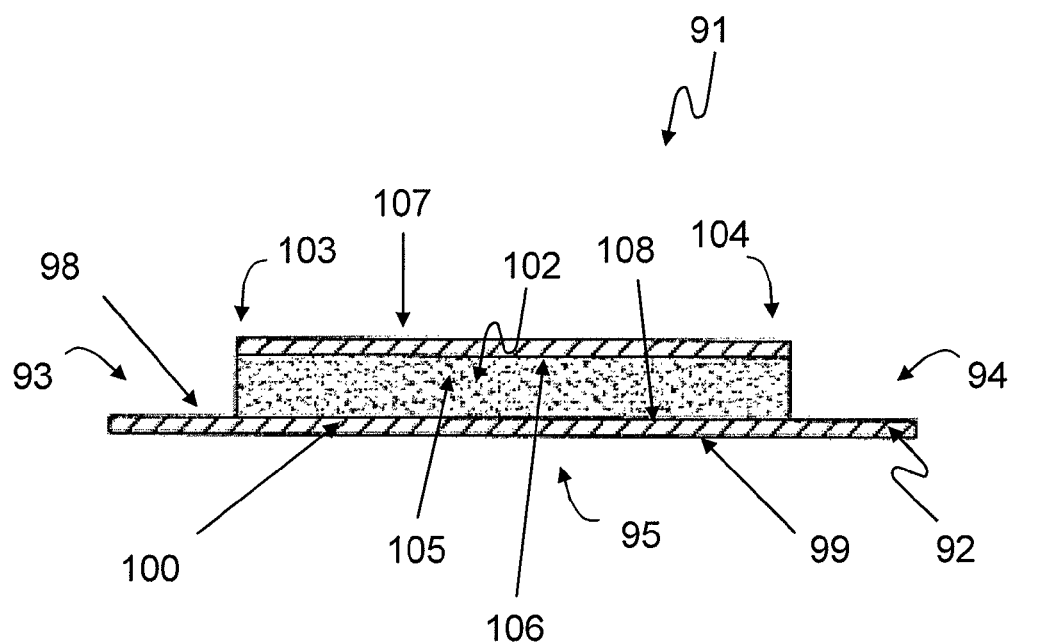
FIG. 28 is cut-away bottom view of a Doyle Shark Nasal Splint according to one aspect of the present invention.
Figure 28:
Figure 28:

Another aspect of the present invention is a nasal septal button 81 comprising a fiber mesh imbedded into one or more portions of its walls. An embodiment of the nasal septal button 81 is shown in FIGS. 22 and 23.

The nasal septal button 81 may comprise a first disc 82 comprising a first surface 83, a second surface 84, and a disc wall 85 therebetween; and a second disc 86 comprising a first surface 87, a second surface 88, and a disc wall 89 therebetween. The nasal septal button 81 may further comprise a connection 90 which extends between and connects the second surface 84 of the first disc 82 and the first surface 87 of the second disc 86. A fiber mesh 12 as described above may be imbedded in one or more portions of the first disc wall 85 and/or one or more portions of the second disc wall 89.

The mesh 12 may be imbedded in various arrangements in the wall of the discs. For instance, the mesh 12 may be imbedded as bands that extend across the disc, or may be imbedded as concentric circles, which is embodied in FIGS. 22 and 23. Alternatively, the mesh 12 may be imbedded throughout the entire disc. The arrangement of imbedded mesh 12 may be the same or different between the first disc 82 and the second disc 86.

The nasal septal button may further comprise a protective coating as described above on one or more portions of the first surface and/or second of the first disc, and/or one or more portions of the first and/or second surface of the second disc.

The connection 90 may be cylindrical, cubic, or other prism-shapes. The dimensions of the connection 90, as well as the first disc 82 and the second disc 86, may be determined by one skilled in the art in consideration of its use as a nasal septal button.

The first surface 83 and second surface 84 of the first disc 82, and the first surface 87 and second surface 88 of the second disc 86 may be flat, convex, or concave in any combination. In the embodiment shown in FIGS. 22 and 23, the first surface 83 of the first disc 82 is convex, the second surface 84 of the first disc 82 is concave, the first surface 87 of the second disc 86 is concave, and the second surface 88 of the second disc 86 is convex.

Further, the first disc 82 and the second disc 86 may be any shape, such as circular, oval, polygonal, etc.

A further aspect of the present invention relates to a nasal splint comprising a fiber mesh imbedded into one or more portions of its walls. Embodiments of the nasal splint 91 are shown in FIGS. 24-28.

The nasal splint 91 may comprise a base 92 comprising a first curved end 93, a second curved end 94, and a middle region 95 therebetween wherein the middle region 95 comprises a first edge 96, a second edge 97, a first surface 98, and a second surface 99, and a base wall 100 therebetween. A fiber mesh 12 may be imbedded in one or more portions of the base wall 100.

The mesh 12 may be imbedded in various arrangements in the base wall 100. For instance, the mesh 12 may be imbedded as bands that extend across the base wall 100, or may be imbedded as bands that are adjacent to the edge of the base wall 100. Alternatively, the mesh 12 may be imbedded throughout the entire base wall 100.

The nasal splint 91 may further comprise one or more holes 101 near the first curved end 93 and/or near the second curved end 94. The holes 101 are for purposes of suturing. The edge of the hole may be level with first surface and/or the second surface, or the edge of the hole may comprise a lip. Also, the base 92 at the site of the holes may have a greater cross-section than other sites of the base 92. The holes 101 provide a secure feature that will allow the physician to pass a suture through, without tearing the silicone device. The suture aids in holding the splint in position. Further, mesh 12 may be imbedded in the base wall 100 around the holes 101.

The nasal splint 91 may further comprise a protective coating 13 as described above that covers one or more portions of the first surface 98 and/or one or more portions of the second surface 99.

The base 91 may be oblong in shape. The first edge 96 and the second edge 97 of the middle region 95 may be curved or substantially straight. The first edge 96 or second edge 97 of the middle region 95 may alternatively comprise portions of various shapes, such as the shape resembling a shark's dorsal fin.

The base 92 may be substantially flat and in the same plane or different planes. For example, the embodiment shown in FIG. 27 comprises a base 92 that is substantially flat but is in two different planes.

The nasal splint 91 may further comprise a tubular structure 102 on the first surface 98. The tubular structure 102 may extend between the first curved end 93 and the second curved end 94 of the base 92. The tubular structure 102 may comprise an open first end 103 and an open second end 104. The tubular structure 102 may also comprise a lumen 105 extending between the first open end 103 and the second open end 104 such that the lumen 105 comprises an inner surface 106, an outer surface 107, and a tubular wall 108 therebetween.

The tubular structure 102 may be of any length, but is limited by the distance between the first curved end 103 and second curved end 104 of the base 92. The tubular structure may also be located at any site between the first edge 96 and the second edge 97 of the base 92. For example, the tubular structure 102 may be adjacent to the first edge 96, may be adjacent to the second edge 97, or anywhere between. The tubular structure 102 may be of a particular size such that it is simultaneously adjacent to both the first edge 96 and the second edge 97 of the base 92.

The first open end 103 and/or the second open end 104 may be curved. Further, the open first end 103 and/or the open second end 104 may also be angled.

The tubular structure 102 between the first open end 103 and the second open end 104 may comprise a curvature. The curvature may be the same as the curvature of the first edge 96.

The mesh 12 may be imbedded in one or more portions of the tubular wall 108 in various location throughout the tubular structure 102 in various patterns or randomly. For example, the mesh 12 may be imbedded in bands around the tubular structure 102, in rows extending along the length of the tubular structure 102, or a combination thereof. The mesh 12 may also be imbedded in the tubular wall 108 in bands circling the tubular structure 102 at the first open end 103 and the second open end 104, or may be in the middle between these ends. Further, the mesh 12 may be imbedded in the tubular walls 108 throughout the entire tubular structure 102.

The tubular structure may additionally comprise a coating on one or more portions of the inner surface 106 and/or the outer surface 107.

The tubular structure may comprise a substantially flat segment (not shown) which extends from the tubular structure 102. The segment may extend towards either the first edge 96 and/or the second edge 97 of the base 92. The segment may be parallel with the base 92.

The nasal splint may also be the Tellez Nasal Splint or the Doyle Shark Nasal Splint comprising fiber mesh 12 imbedded in walls of the splint. The embodiment of FIGS. 24 and 25 relate to the Tellez Nasal Splint, while the embodiment of FIGS. 26-28 relate to the Doyle Shark Nasal Splint. Importantly, these represent examples of nasal splints, and the present invention encompasses nasal splints of various forms and shapes, in which a fiber mesh is embedded in the wall therein.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

What is claimed is:

1. A device for airway or esophageal management comprising a tubular arm comprising:
   (i) a first open end;
   (ii) a second open end;
   (iii) a lumen extending therethrough having an inner surface and an inner circumference;
   (iv) an outer surface;
   (v) an outer circumference;
   (vi) a tubular wall between the inner surface and outer surface; and
   (vii) a longitudinal axis through the center of the lumen of the first tubular arm,
   wherein the tubular wall comprises one or more portions; and
   wherein the one or more portions in which a fiber mesh is imbedded, and one or more portions in the fiber mesh is not imbedded of the tubular wall in which the fiber mesh is imbedded is not different in thickness from portions of the tubular wall in which the fiber mesh are not imbedded.

2. The device of claim 1, wherein the fibers are woven.

3. The device of claim 2, wherein the woven fibers are polyester or nylon.

4. The device of claim 1, further comprising a protective coating on one or more portions of the inner surface, one or more portions on the outer surface, or a combination thereof.

5. The device of claim 1, wherein the protective coating is a polymeric coating.

6. The device of claim 5, wherein the polymer is parylene.

7. The device of claim 1, further comprising a means to prevent movement or displacement of the device.

8. The device of claim 7, wherein the means to prevent movement or displacement of the device is one or more rings around the circumference of the device, one or more posts that extend outwardly from the outer surface of the device, or a combination thereof.

9. The device of claim 8, wherein the one or more rings are located on the first open end of the device, the second open end of the device, between the first open end and the second open end of the device, or any combination thereof.

10. The device of claim 8, wherein the posts are cylindrical, cubic, pyramidal, or prism-shaped.

11. The device of claim 10, wherein the posts are distributed randomly or in a pattern along the outer surface of the device.

12. The device of claim 1, wherein the outer circumference is constant throughout the device.

13. The device of claim 1, wherein the outer circumference is not constant throughout the device.

14. The device of claim 13, wherein the outer circumference is greater near the first open end and the second open end.

15. The device of claim 1, wherein the inner circumference is constant throughout the device.

16. The device of claim 1, wherein the inner circumference varies throughout the device.

17. The device of claim 1, further comprising a funnel attached to the second open end.

18. The device of claim 1, further comprising a second tubular arm, wherein the second tubular arm comprises:
   (i) a first open end;
   (ii) a second open end;
   (iii) a lumen extending therethrough having an inner surface and an inner circumference;
   (iv) an outer surface;
   (v) an outer circumference;
   (vi) a tubular wall between the inner surface and outer surface; and
   (vii) a longitudinal axis through the center of the lumen of the second tubular arm,
   wherein the second tubular arm is connected to the first tubular arm by the first open end of the second tubular arm to between the first open end and the second open end of the first tubular arm.

19. The device of claim 18, wherein the lumen of the first tubular arm and the lumen of the second tubular arm is continuous.

20. The device of claim 18, further comprising a fiber mesh imbedded in one or more portions of the tubular wall of the second tubular arm.

21. The device of claim 20, wherein the fibers are woven.

22. The device of claim 21, wherein the woven fibers are polyester or nylon.

23. The device of claim 18, further comprising a protective coating on one or more portions of the inner surface, one or more portions on the outer surface, or a combination thereof, of the second tubular arm.

24. The device of claim 23, wherein the protective coating is a polymeric coating.

25. The device of claim 24, wherein the polymer is parylene.

26. The device of claim 18, wherein the second tubular arm further comprises a plug that inserts into the second end of the second tubular arm.

27. The device of claim 26, wherein the plug fits tightly adjacent to the inner surface of the second end of the second tubular arm.

28. The device of claim 18, wherein the longitudinal axis of the first tubular arm forms an angle with the longitudinal axis of the second tubular arm.

29. The device of claim 28, wherein the angle is between 0° and 180°.

30. The device of claim 28, wherein the angle is 90°.

31. The device of claim 1, wherein the second end of the first tubular arm is bifurcated into a first tubular diagonal arm and a second tubular diagonal arm, wherein each arm comprises:
   (i) a first open end;
   (ii) a second open end;
   (iii) a lumen extending therethrough having an inner surface and an inner circumference;
   (iv) an outer surface;
   (v) an outer circumference;
   (vi) a tubular wall between the inner surface and outer surface, and
   (vii) a longitudinal axis through the center of the lumen of each diagonal arm.

32. The device of claim 31, wherein the lumen in the diagonal arms is continuous with the lumen of the device.

33. The device of claim 31, wherein the lengths of the first diagonal arm and the second diagonal arm are equal.

34. The device of claim 31, wherein the lengths of the first diagonal arm and the second diagonal arm are unequal.

35. The device of claim 31, further comprising a fiber mesh imbedded in one or more portions of the tubular wall of the second tubular arm.

36. The device of claim 35, wherein the fibers are woven.

37. The device of claim 36, wherein the woven fibers are polyester or nylon.

38. The device of claim 31, further comprising a protective coating on one or more portions of the inner surface, one or more portions on the outer surface, or a combination thereof, of the second tubular arm.

39. The device of claim 38, wherein the protective coating is a polymeric coating.

40. The device of claim 39, wherein the polymer is parylene.

41. The device of claim 31, wherein the longitudinal axis of the first tubular arm forms a first angle with the longitudinal axis of the first diagonal arm and wherein the longitudinal axis of the first tubular arm forms a second angle with the longitudinal axis of the second diagonal arm.

42. The device of claim 41, wherein the first angle and the second angle are equal.

43. The device of claim 41, wherein the first angle and the second angle are unequal.

44. The device of claim 31, further comprising a second tubular arm, wherein the second tubular arm comprises:
   (i) a first open end;
   (ii) a second open end;
   (iii) a lumen extending therethrough having an inner surface and an inner circumference;
   (iv) an outer surface;
   (v) an outer circumference;
   (vi) a tubular wall between the inner surface and outer surface; and
   (vii) a longitudinal axis through the center of the lumen of the second tubular arm,
   wherein the second tubular arm is connected to the first tubular arm between the first open end and the second open end of the first tubular arm.

45. The device of claim 44, wherein the lumen of the first tubular arm and the lumen of the second tubular arm is continuous.

46. The device of claim 44, further comprising a fiber mesh imbedded in one or more portions of the tubular wall of the second tubular arm.

47. The device of claim 46, wherein the fibers are woven.

48. The device of claim 47, wherein the woven fibers are polyester or nylon.

49. The device of claim 44, further comprising a protective coating on one or more portions of the inner surface, one or more portions on the outer surface, or a combination thereof, of the second tubular arm.

50. The device of claim 49, wherein the protective coating is a polymeric coating.

51. The device of claim 50, wherein the polymer is parylene.

52. The device of claim 44, wherein the longitudinal axis of the first tubular arm forms an angle with the longitudinal axis of the second tubular arm.

53. The device of claim 52, wherein the angle is between 0° and 180°.

54. The device of claim 52, wherein the angle is 90°.

55. The device of claim 1, wherein the fiber mesh is surrounded by the tubular wall.

56. The device of claim 1, wherein the fiber mesh is flexible.

57. The device of claim 1, wherein the fiber mesh does not hinder flexibility of the device or the tubular wall.

* * * * *